(12) United States Patent
Okuda

(10) Patent No.: US 11,278,045 B2
(45) Date of Patent: Mar. 22, 2022

(54) METHOD FOR PRODUCING NUCLEIC ACID SEASONING

(71) Applicant: AMANO ENZYME INC., Nagoya (JP)

(72) Inventor: Keita Okuda, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 0 days.

(21) Appl. No.: 16/338,711

(22) PCT Filed: Oct. 4, 2017

(86) PCT No.: PCT/JP2017/036193
§ 371 (c)(1),
(2) Date: Apr. 2, 2019

(87) PCT Pub. No.: WO2018/066617
PCT Pub. Date: Apr. 12, 2018

(65) Prior Publication Data
US 2019/0223480 A1    Jul. 25, 2019

(30) Foreign Application Priority Data

Oct. 7, 2016 (JP) .............................. JP2016-199543

(51) Int. Cl.
| | |
|---|---|
| *A23L 27/23* | (2016.01) |
| *A23L 33/145* | (2016.01) |
| *C12N 9/78* | (2006.01) |
| *C12N 9/24* | (2006.01) |
| *A23L 31/15* | (2016.01) |
| *C12N 15/09* | (2006.01) |
| *C12N 9/16* | (2006.01) |

(52) U.S. Cl.
CPC .............. *A23L 27/23* (2016.08); *A23L 31/15* (2016.08); *A23L 33/145* (2016.08); *C12N 9/2497* (2013.01); *C12N 9/78* (2013.01); *C12N 9/16* (2013.01); *C12N 15/09* (2013.01); *C12Y 302/02001* (2013.01); *C12Y 305/04006* (2013.01)

(58) Field of Classification Search
CPC ........ A23L 27/23; A23L 33/145; A23L 31/15; C12N 9/2497; C12N 9/16; C12N 9/78; C12Y 302/02001; C12Y 305/04006
USPC .......................................................... 426/62
See application file for complete search history.

(56) References Cited

U.S. PATENT DOCUMENTS

2004/0258800 A1* 12/2004 Tsuruhami .............. A23L 31/15
    426/62
2005/0054058 A1    3/2005 Ikeuchi et al.

FOREIGN PATENT DOCUMENTS

| EP | 0753572 A1 | 1/1997 |
|---|---|---|
| EP | 0825261 A2 | 2/1998 |

(Continued)

OTHER PUBLICATIONS

Kuninada, A. Studies on the decomposition of nucleic acids by microorganisms. J. Agric. Chem. Soc. Japan. 23: 281-288 (Year: 1959).*

(Continued)

*Primary Examiner* — Hamid R Badr
(74) *Attorney, Agent, or Firm* — Locke Lord LLP

(57) ABSTRACT

It is an object of the present invention to provide a nucleic acid-based seasoning improved in taste. There is provided a method for producing a nucleic acid-based seasoning, which includes a step of treating a ribonucleotide-containing material with a nucleosidase.

17 Claims, 20 Drawing Sheets

Specification includes a Sequence Listing.

(56) References Cited

FOREIGN PATENT DOCUMENTS

| EP | 1 479 299 A1 | 11/2004 | | |
|---|---|---|---|---|
| EP | 3 120 714 A1 | 1/2017 | | |
| EP | 3502249 A1 | 6/2019 | | |
| JP | 1994-113789 A | 4/1994 | | |
| WO | 2003/055333 A1 | 7/2003 | | |
| WO | 2015/141531 A1 | 9/2015 | | |
| WO | WO-2015141531 A1 * | 9/2015 | ........... | A23L 33/145 |
| WO | 2018/034289 A1 | 2/2018 | | |

OTHER PUBLICATIONS

WO 2015/141531—Machine Translation. (Year: 2015).*
Basant K. Dwivedi et al., "Meat flavor", Critical Reviews in Food Science & Nutrition, vol. 5, No. 4, Jan. 1, 1975, pp. 487-535. (cited in th Apr. 9, 2020 Search Report issued for EP17858454.6).
Supplementary European Search Report dated Apr. 9, 2020, issued for the European Patent Application No. 17858454.6.
International Search Report dated Dec. 26, 2017, issued for PCT/JP2017/036193.
Frozen Food Technology Research, May 1996, No. 32, pp. 1-35 (cited in the Oct. 19, 2021 Notice of Reasons for Refusal issued for JP543946/2018, see p. 2 of the English translation of the JP Notice of Reasons for Refusal).
T. Mouri et al., "Studies on Nucleic Acid Related Substances in Foodstuffs-IX Nucleic Acid Degrading Enzymes of Mushroom," Fermentation Engineering Magazine, 1966, vol. 44, No. 12, pp. 231-240 and an English abstract thereof. (cited in the Oct. 19, 2021 Notice of Reasons for Refusal issued for JP543946/2018).
T. Mouri et al., "Nucleic acid Decomposing Enzymes of Some Mushrooms," Research Report, 1970, No. 9, pp. 196-209 and an English abstract thereof (cited in the Oct. 19, 2021 Notice of Reasons for Refusal issued for JP543946/2018).
T. Mouri et al., "Studies on Nucleic Acid Related Substances in Foodstuffs, (IV) Changes of Nucleic Acid Related Substances during the Processing of Edible Mushrooms (Part I)," Fermentation Engineering Magazine, 1965, vol. 43, No. 5, pp. 335-343 and an English abstract thereof, (cited in the Oct. 19, 2021 Notice of Reasons for Refusal issued for JP543946/2018).
Notice of Reasons for Refusal dated Oct. 19, 2021, issued in the corresponding JP Patent Application No. 543946/2018 and an English translation thereof.

* cited by examiner

|  |  | Peak 1 | Peak 2 | Peak 3 |
|---|---|---|---|---|
| SDS-PAGE molecular weight | Sugar chain present | About 50 kDa | About 50 kDa | About 53 kDa |
|  | Sugar chain absent | About 40 kDa | About 40 kDa | About 48 kDa |
| Gel filtration molecular weight | | About 230 kDa | About 230 kDa | About 126 kDa |
| N-terminal amino acid sequence | | ADKHYAIMDNDWYTA | ADKHYAIMDNDWYTA | VETKLIFLT |
|  |  | SEQ ID NO: 7 | SEQ ID NO: 8 | SEQ ID NO: 9 |

*Fig. 5*

| Probe sequence | PN1 | GAGGATCCCGAAACCTTCCTACGTGTCAAGGAGGTCGTTGTGATGGGTGGAGCAATCAACCAGCCTGGAAATGTATGAACCCGTCG
AAACACCCATTTGATAATAAGTCATTAACGCGGATTGACTAGGTCACCCCGGTTGACTAGAATTCAACGCCTACGCAGACGCCGTTGCA
GCTGCGCGAGTCTTTGCGCTGACATCACCTAATCCCAACTCGACTCTACCACCGAGTCGACTAGTCCCACTACTTGGCCTGTACCCTGCA
AAGCTCAGCCGACAATTGACTCTGCGTCTCGCCTCTCTTCCCGCGTGGACATCACCCTGGGACATCAACCTGTCCCGGGGCCAATTCCGCCAAGCA
GTTGAGCCTCTCCTCGGCAACAGGCTCACCCTGAGTCTGAATGGGTGACAGCATTCATGGGACACAACGTTCCGAACCCTGGAACGCCTG
CACCCCGGCTCGCCATGAAGGGGGATGAAGCCTGAGTCTCCACGACCCCTGTGTCTGTGTGGTATGCCCTTACAGGCAGAGGATTCGCAC
TGGGACTCCCTCGCCCAATTCCCCAGAGAGGACATTCGTGTTGAGACGATTGGGCC SEQ ID NO: 18 |
|---|---|---|

| Probe sequence | PN2 | AGACACCGGCAAACACCTGGCCAGCCTGGCTCCTCAAGGTCGGCTCGGGCAACCGGTTCCCAGGGTGAGTGCCAAGCTGGCAACTTGAGCTGTATCCCGGAGGGTGCCATGGAGGGTGC
CCCAGGCTCGACATGGGCGGCTCATCAACACCCCAAACCGGTTCCAGGGGTGGAAATGGTTCATGGCAAGCTGCCATGGAGGGTGC
TTTTGCGCCGGAGAACAAGACTCTCGAGGCAAGGAGGAACAGAACATCTGCTGCCAACTTCATGGTCGAGATGGTGCACAAGTACCCCGGCCAGGT
GGAAGGGTTCCCCAAGGAGCCCTGCTGGAGCCGTGACCAATGTTGCCGCTGGCTGTGCCATGGATCCCCAGTTTGCATCTCTGGCTAAGGAGTTGGT
CTCGATCTACTCTGCTGGAGCGTCGATTTGAATATGCTCCAGGCCACTGGAAGTGTCTTGCTGCTGATCTTCAATCTG SEQ ID NO: 19 |
|---|---|---|

*Fig. 6*

| | PN1 |
|---|---|
| Genomic sequence (SEQ ID NO: 4) | ATGGCACCTAAGAAAATCATCATTGACACTGACCCCGGTAAGTTGCCTATACATAACTGAAGATATCTACTCCTAGACATG<br>CTAATGAATGATTAGGGTATCGATGACATCCTGGCACTGCTGCTGGCTCTGTCATCTAAGCCAGAGGATGTTGAGATTCT<br>ACTTATCTCTTTAACATTTGGAAACATTGAGGTGAAGAAGTGAGTGCTACCTTTGTGAAAGTCAACTCAGAAACGAGTTC<br>AGCCTATTTATTTCGTTAGAGCTGTCTTCGAAATGTGGTCTCCATGTTTCATATCCTCGAGCGCGAGATCCAGTGGCGTC<br>GTGGTAACGGCAAGTCCGAAGGCTATGGCACTATGCGTGCTTTCCGCCCAGTAGTAGCCGTGGGAGCGGAAGATCCCTTG<br>GAAGACCAGAAGATGCTCGCTGATTATTTCCGTAAGTCCTTTGTGGTTTTGAAAGTCAATCACGTCGCTGAGAATTACCC<br>CGCAGATGGAACCGATGGCCTTGGTGGCATCCATGCTAGTGTAGGCTAAACGCCCACCTTATTCGACCAATGATGTACCC<br>ATTTTCTAACACTATCTGGACAGCACCCACATCTCACTCCAAGCAAGGCTGGGAGCATCTATTCACCCCGGCGTGGAT<br>CCCCAGGGGATCGAGCCTGTGCAAACGGGAGCTGGTCCCGGCGACCATTCCTTTATCCCATCAAGACTACCTGCACACAA<br>GGAGATTCTTCGTGCACTGCGCCAGAATGAGCCTGACACCGTGACTCTCGTGGCGGTTGGTCCACTGACCAACTTGGCCT<br>TGGCAGCAGCAGAGGATCCCGAAACCTTCCTACGTGTCAAGGAGGTCGTTGTGATGGGTGGAGCAATCAACCAGCCTGGA<br>AATGTATGAACCCGTCGAAACACGCATTTGATAATAAGTCATTAACCGCGATTGACTAGGTCACCCCCGTTGGAGAATT<br>CAACGGCTACGCAGCACGCGGTTGCAGCTGCGCGGAGTCTTTGCGCTGACATCACCTAATCCCAACTCGACTCTACCACCGA<br>CCACGAGTCCACTACTTGGCCTGTACCCTGCAAAGCTCAGCCGACAATTGACTCTGCGTCTCTTCGCGCTGGACATCACC<br>CTGCGCATAACCTGTCCCGCGGCCAATTCCGCCAAGCAGTTGAGCCTCTCCTCGCAACAGGCTCACCCCTCGCTGAATG<br>GGTGACAGGATTCATGGGACACACGTTCCGAACCCTGGAACGCCTGCACCCCGGCCATGAGGCGATGAAGCCCAGCTGA<br>GTCTCCACGACCCTGTCTGTGTGTGGTATGCCCTTACAGCAGAGGATTCGCACTGGACTCCCTCCGCCAATTCCCCAGAG<br>GACATTCGTGTTGAGACATTGGGCCAGTGGACGCGTGGTATGTGCGTAATCGATGGCCGAAACCGCCATAAGATTGATGG<br>CGACGAGGAAAGCTCGAGTGATCATGGTCTGTGGTTGAGTGCTCGTGCAGGAAACCGGATTTTGCGAATGGATGGATCGC<br>CAGCCGAACACACGTTCGGCAAGATCCTCATCGATAGAATCTTCCACTAA |
| | PN2 |
| Genomic sequence (SEQ ID NO: 6) | ATGCATTTCCCTGTTTCATTGCCGCTGTTGTGCGGCTCTTTGCTGCCTCTCATCACCGGCACCCTGGCAGTGCCCAAGGC<br>CTCGCGTGCCGACAAGCACTATGCCATCATGGACAATGATTGGTACACAGCGGGTTTCGTGCCTTACCTGATCGCCCTGG<br>ATGGCGATGTGGAGGTTCTGGGCCTAGCCTCTGGTTAGTGTTGATCCGCATCCATACCGGTTTTCCTTCAAGGTCTGCAG<br>TGCTAAGCTTCCATGTCATATCAGACACCGCAAACACCTGGCAGCCTCAGGTCGCTCTGCACGGCTGTCGCAACTCTGAAG<br>CTGGCAACTTGAGCTGTATCCCCGTTTACCCAGGCTCGACATGCCGCTCATCAACACCCCCAACCGCTTCCAGGCGTGG<br>GAAATGGTTCATGGCAAGCTGCCATGGGAGGGTGCTTTTGCGCCGGAGAACAAGACTGTCGAGGCCGAGGGTAACGATCC<br>TACCTCTGGCAAGCCCAACCGTATCGTCAAGGCGCTTTCAAGGAAGGGTTCCCCAAGGGCAAGCCCGAGAACAGAACAT<br>CTGCTGCCAACTTCATGGTCGAGATGGTGCACAAGTACCCCGGCAGGTCTCGATCTGCTGGAGCCCTGACCAAT<br>GTTGCGCTGGCTGTGCCGATGGATCCCCAGTTTGCATCTCTGGCTAAGGAGTTGGTTATCATGGCTGGATACGTCGATTT<br>GAATATGCTCGAGGCCACTGGAAGTGTCTTGCTGGCTGATCTTCAATCTGATGTATGTTTCATTCCCGGCTTCTATCAGC<br>TGTGTTCATCTGCTAACTTCTCTTTAGATCAACTTGATGATTGATCCCGAGGCCTCCAAGATCGCATTGACTGCCGAATT<br>CGCCAATATGACCATCGCGGTAACGTCGCCAACCAGGTCTTTCCTACCAAGGAGTTCGTCGACGAGATCCCCTCCGTTC<br>CAAAGCCCTACAGCAAGCTCTTCCACGACTACTACGATCTGTCCTTCCCTTCTGGGATGAGACGGCTGCCGCGCTGATG<br>GTTGACCCTAGTGTTGCTACCAACCAGACCTCTGGTGAGTTTAATCTCGGATTGACACTTGTATGAACAAATCTAACAGC<br>TTATAGTCTTCCTCGACGTGGATACCGCTTATGGTAGCCCGAACTATGGTAACATTCACGTTTACCAGAACGCTCTTGCC<br>CCTGTTGGTATCCGGGAGGTCAACTTTGTCTTCCAGGTTGATGGGATAGACTTAAGCAGCGCATCAAGCACTCTCTGCA<br>GTACCCGCAAGTCATGCGCCGACGTGAGAAATGAGCGTTGA |

Fig. 7

| | PN1 |
|---|---|
| cDNA sequence (SEQ ID NO: 3) | ATGGCACCTAAGAAAATCATCATTGACACTGACCCGGGTATCGATGACATCCTGGCACTGCTGCTGGCTGTGTCATCTAAGCCAGAGGATGTTGAGATTCTACTTATCTCTTTAACATTTGGAAACATTGAGGTGAAGAACTGTCTTGGAAATGTGGTCTCCATGTTTCATATCCTCGAGGCGGAGATCCAGTGGCGTCGTGGTAACGGCAAGTCCGAAGGCTATGGCACTATGCGTGCTTTCCGGCCAGTAGTAGCCGTGGGAGCGGAAGATCCCTTGGAAGACCAGAAGATGCTCGCTGATTATTTCCATGGAACCGATGGCCTTGGTGGCATCCATGCTAGTCACCCACATCTCACTCCAAGGCAAGGCCTGGGAGCATCTATTCAGCCCGGCCGTGGATCGGCAGGGATCGAGCCTGTGCAAACGGGAGCTGGTCCGGCGACCATTCCTTTATCGCATCAAGACTACCTGCACACAAGGAGATTCTTCGTGCACTGCGCCAGAATGAGCCTGACACCGTGACTCTCGTGGCCGGTTGGTCCACTGACCAACTTGGCCTTGGCAGCAGCAGGATCCCGAAACCTTCCTACCGTGTCAAGGAGGTCGTTGTGATGGGTGGAGCAATCAACCAGCCTGGAAATGTCACGCCCGTTGGAGAATTCAACGCCTAGGCAGACGCCGTTGCAGCCTGCGCGAGTCTTTGCGCTGACATCACCTAATCCCAACTCGACTCTACCACCGACCACGAGTCCACTACTTGGCCTGTACCCTGCAAAGCTCAGCCGACAATTGACTCTGCGTCTCTTCCCGCTGGACATCACCCTGCGCGCATAACCTGTCCGCGCGGCCAATTCCGCCAAGCAGTTGAGGCTCTCCTCGCAACAGGCTCACCCCTCGCTGAATGGGTGACAGCATTCATGGGACACACGTTCCGAACCCTGGAACGGCTGCACCCGGGCCATGAGGGCGATGAAGCCCAGCTGAGTCTCCACGACCCTGTCTGTGTGTGGTATGCCCTTACAGCAGAGGATTCGCACTGGACTCCCTCCGCCAATTCCCCAGAGGACATTCGTGTTGAGACATTGGGCCAGTGGACGCGTGGTATGTGCGTAATCGATGGCCGAAACCGCCATAAGATTGATGGCGACGAGGAAAGCTCGAGTGATCATGGTCTGTGGTTGAGTGCTCGTGCAGGAAACGGCATTTTGCGAATGGATGGATCGCCAGCCGAACACACGGTTCGGCAAGATCCTCATCGATAGAATCTTCCACTAA |
| | PN2 |
| cDNA sequence (SEQ ID NO: 5) | ATGCATTTCCCTGTTTCATTGCCGGCTGTTGTGGCGGCTCTTTGCTGCCTCTGTCATCACCGGGACCCTGGCAGTGCCCAAGGCCTCGGGTGCCGACAAGCACTATGCCATCATGGACAATGATTGGTACACAGCGGGTTTCGTGCCTTACCTGATCGCCCTCGATGGCGATGTGGAGGTTCTGGGCCTAGCCTCTGACAGCGGCAAACACCTGGCAGCCTCAGGTCGCTCTGCACGCTGTCGGCAACTCTGGAAGCTGGCAACTTGAGCTGTATCCCCCTTTACCCAGGCTCGACATGGCCGCTCATCAACACCCCCAACCGCTTCCAGGCGTGGGAAATGGTTCATGGCAAGCTGCCATGGAGGGTGCTTTTGCGCGGGAGAACAAGACTCTCGAGGCCGAGGGTAACGATCCTACCTCTGGCAACCCCAACCGTATCGTCAAGGCCGCTTTCAAGGAAGGGTTCCCCAAGGGCAAGCCCGAGAAACAGAACATCTGCTGCCAAGTTCATGGTCGAGATGGTGCACAAGTACCCCGGCCAGGTCTCGATCTAGTCTGCTGGAGCCCTGACCAATGTTGCGCTGGCTGTGCGCATGGATCCCAGTTTGCATCTCTGGCTAAGGAGTTGGTTATCATGGGTGGATACGTCGATTTGAATATGCTCCAGGCCACTGGAACTGTCTTGCTGGCTGATCTTCAATCTGATATCAACTTGATGATTGATCCCGAGACTCCAAGATCGCATTGACTGCCGAATTGCCAATATCACCATCGGCGGTAACGTCGCCAACCAGGTCTTTCCTACCAAGGAGTTCGTCGACGAGATCGCCTCCGTTCCAAACCCCTACAGCAAGCTCTTCCAGGACTACTACGATCTGTCCTTCCCCTTCTGGGATGAGACGGCTGCCGCGCTGATGGTTGACCCTACTCTTGCTACCAACCAGACCTCTGTCTTCCTCGACGTGGATACCGCTTATGGTAGCCCAACTATGGTAACATTCACGTTTACCAGAAGGCTCTTGCCCCTGTTGGTATCGGGAGGTCAACTTTGTCTTCCAGGTTGATGGGGATAGACTTAAGCAGCGCATCAAGCACTCTCTGCAGTACCCCAAGTCATGCGCCGACCTGAGAAATGAGCGTTGA |

*Fig. 8*

PN1 (peak 3) (SEQ ID NO: 1)

MAPKKIIIDTDPGIDDILALLLALSSKPEDVEILLISLTFGNIEVKNCLRNVVSMFHILE
REIQWRRGNGKSEGYGTMRAFRPVVAVGAEDPLEDQKMLADYFHGTDGLGGIHASHPHLT
PSKAWEHLFTPAVDPQGIEPVQTGAGPGDHSFIPSRLPAHKEILRALRQNEPDTVTLVAV
GPLTNLALAAAEDPETFLRVKEVVVMGGAINQPGNVTPVGEFNAYADAVAAARVFALTSP
NPNSTLPPTTSPLLGLYPAKLSRQLTLRLFPLDITLRHNLSRGQFRQAVEPLLATGSPLA
EWVTAFMGHTFRTLERLHPGHEGDEAQLSLHDPVCVWYALTAEDSHWTPSANSPEDIRVE
TLGQWTRGMCVIDGRNRHKIDGDEESSSDHGLWLSARAGNRILRMDGSPAEHTFGKILID
RIFH*

PN2 (peaks 1 and 2) (SEQ ID NO: 2)

MHFPVSLPLLCGSLLPLITGTLAVPKASRADKHYAIMDNDWYTAGFVPYLIALDGDVEVL
GLASDTANTWQPQVALHAVATLEAGNLSCIPVYPGSTWPLINTPNRFQAWEMVHGKLPWE
GAFAPENKTLEAEGNDPTSGNPNRIVKAAFKEGFPKGKPENRTSAANFMVEMVHKYPGQV
SIYSAGALTNVALAVRMDPQFASLAKELVIMGGYVDLNMLQATGSVLLADLQSDINLMID
PEASKIALTAEFPNITIAGNVANQVFPTKEFVDEIASVPNPYSKLFHDYYDLSFPFWDET
AAALMVDPTLATNQTSVFLDVDTAYGSPNYGNIHVYQKALAPVGIREVNFVFQVDGDRLK
QRIKHSLQYPKSCADLRNER*

*Fig. 9*

|  | PN1 | PN2 |
|---|---|---|
| Number of bases (cDNA) | 1,275 bp | 1,143 bp |
| Number of introns | 5 | 3 |
| Amino acid length | 424 aa | 380 aa |
| Estimated molecular weight | 46,400 | 41,600 |
| Estimated pI | 5.7 | 5.0 |

*Fig. 10*

| Panelist | A | B | C | D | E | F | G | H |
|---|---|---|---|---|---|---|---|---|
| Evaluation | ○ | ○ | ○ | ○ | ○ | ○ | ○ | ○ |

○: Umami increased in nucleosidase-added group

△: Unchanged

×: Umami decreased in nucleosidase-added group

*Fig. 20*

SEQUENCE LISTING

```
<160> NUMBER OF SEQ ID NOS: 19

<210> SEQ ID NO 1
<211> LENGTH: 424
<212> TYPE: PRT
<213> ORGANISM: Penicillium multicolor

<400> SEQUENCE: 1

Met Ala Pro Lys Lys Ile Ile Ile Asp Thr Asp Pro Gly Ile Asp Asp
1               5                   10                  15

Ile Leu Ala Leu Leu Leu Ala Leu Ser Ser Lys Pro Glu Asp Val Glu
            20                  25                  30

Ile Leu Leu Ile Ser Leu Thr Phe Gly Asn Ile Glu Val Lys Asn Cys
        35                  40                  45
```

Leu Arg Asn Val Val Ser Met Phe His Ile Leu Glu Arg Glu Ile Gln
    50                  55                  60

Trp Arg Arg Gly Asn Gly Lys Ser Glu Gly Tyr Gly Thr Met Arg Ala
65                  70                  75                  80

Phe Arg Pro Val Ala Val Gly Ala Glu Asp Pro Leu Glu Asp Gln
                85                  90                  95

Lys Met Leu Ala Asp Tyr Phe His Gly Thr Asp Gly Leu Gly Gly Ile
                100                 105                 110

His Ala Ser His Pro His Leu Thr Pro Ser Lys Ala Trp Glu His Leu
            115                 120                 125

Phe Thr Pro Ala Val Asp Pro Gln Gly Ile Glu Pro Val Gln Thr Gly
130                 135                 140

Ala Gly Pro Gly Asp His Ser Phe Ile Pro Ser Arg Leu Pro Ala His
145                 150                 155                 160

Lys Glu Ile Leu Arg Ala Leu Arg Gln Asn Glu Pro Asp Thr Val Thr
                165                 170                 175

Leu Val Ala Val Gly Pro Leu Thr Asn Leu Ala Leu Ala Ala Ala Glu
            180                 185                 190

Asp Pro Glu Thr Phe Leu Arg Val Lys Glu Val Val Met Gly Gly
                195                 200                 205

Ala Ile Asn Gln Pro Gly Asn Val Thr Pro Val Gly Glu Phe Asn Ala
210                 215                 220

Tyr Ala Asp Ala Val Ala Ala Arg Val Phe Ala Leu Thr Ser Pro
225                 230                 235                 240

Asn Pro Asn Ser Thr Leu Pro Pro Thr Thr Ser Pro Leu Leu Gly Leu
                245                 250                 255

Tyr Pro Ala Lys Leu Ser Arg Gln Leu Thr Leu Arg Leu Phe Pro Leu
                260                 265                 270

Asp Ile Thr Leu Arg His Asn Leu Ser Arg Gly Gln Phe Arg Gln Ala
            275                 280                 285

Val Glu Pro Leu Leu Ala Thr Gly Ser Pro Leu Ala Glu Trp Val Thr
    290                 295                 300

Ala Phe Met Gly His Thr Phe Arg Thr Leu Glu Arg Leu His Pro Gly
305                 310                 315                 320

His Glu Gly Asp Glu Ala Gln Leu Ser Leu His Asp Pro Val Cys Val
                325                 330                 335

Trp Tyr Ala Leu Thr Ala Glu Asp Ser His Trp Thr Pro Ser Ala Asn
                340                 345                 350

Ser Pro Glu Asp Ile Arg Val Glu Thr Leu Gly Gln Trp Thr Arg Gly
            355                 360                 365

Met Cys Val Ile Asp Gly Arg Asn Arg His Lys Ile Asp Gly Asp Glu
370                 375                 380

Glu Ser Ser Ser Asp His Gly Leu Trp Leu Ser Ala Arg Ala Gly Asn
385                 390                 395                 400

Arg Ile Leu Arg Met Asp Gly Ser Pro Ala Glu His Thr Phe Gly Lys
                405                 410                 415

Ile Leu Ile Asp Arg Ile Phe His
                420

<210> SEQ ID NO 2
<211> LENGTH: 380
<212> TYPE: PRT
<213> ORGANISM: Penicillium multicolor

<400> SEQUENCE: 2

```
Met His Phe Pro Val Ser Leu Pro Leu Leu Cys Gly Ser Leu Leu Pro
1               5                   10                  15

Leu Ile Thr Gly Thr Leu Ala Val Pro Lys Ala Ser Arg Ala Asp Lys
            20                  25                  30

His Tyr Ala Ile Met Asp Asn Asp Trp Tyr Thr Ala Gly Phe Val Pro
        35                  40                  45

Tyr Leu Ile Ala Leu Asp Gly Asp Val Glu Val Leu Gly Leu Ala Ser
    50                  55                  60

Asp Thr Ala Asn Thr Trp Gln Pro Gln Val Ala Leu His Ala Val Ala
65              70                  75                  80

Thr Leu Glu Ala Gly Asn Leu Ser Cys Ile Pro Val Tyr Pro Gly Ser
                85                  90                  95

Thr Trp Pro Leu Ile Asn Thr Pro Asn Arg Phe Gln Ala Trp Glu Met
                100                 105                 110

Val His Gly Lys Leu Pro Trp Glu Gly Ala Phe Ala Pro Glu Asn Lys
        115                 120                 125

Thr Leu Glu Ala Glu Gly Asn Asp Pro Thr Ser Gly Asn Pro Asn Arg
    130                 135                 140

Ile Val Lys Ala Ala Phe Lys Glu Gly Phe Pro Lys Gly Lys Pro Glu
145                 150                 155                 160

Asn Arg Thr Ser Ala Ala Asn Phe Met Val Glu Met Val His Lys Tyr
                165                 170                 175

Pro Gly Gln Val Ser Ile Tyr Ser Ala Gly Ala Leu Thr Asn Val Ala
            180                 185                 190

Leu Ala Val Arg Met Asp Pro Gln Phe Ala Ser Leu Ala Lys Glu Leu
        195                 200                 205

Val Ile Met Gly Gly Tyr Val Asp Leu Asn Met Leu Gln Ala Thr Gly
    210                 215                 220

Ser Val Leu Leu Ala Asp Leu Gln Ser Asp Ile Asn Leu Met Ile Asp
225                 230                 235                 240

Pro Glu Ala Ser Lys Ile Ala Leu Thr Ala Glu Phe Pro Asn Ile Thr
                245                 250                 255

Ile Ala Gly Asn Val Ala Asn Gln Val Phe Pro Thr Lys Glu Phe Val
            260                 265                 270

Asp Glu Ile Ala Ser Val Pro Asn Pro Tyr Ser Lys Leu Phe His Asp
        275                 280                 285

Tyr Tyr Asp Leu Ser Phe Pro Phe Trp Asp Thr Ala Ala Ala Leu
    290                 295                 300

Met Val Asp Pro Thr Leu Ala Thr Asn Gln Thr Ser Val Phe Leu Asp
305                 310                 315                 320

Val Asp Thr Ala Tyr Gly Ser Pro Asn Tyr Gly Asn Ile His Val Tyr
                325                 330                 335

Gln Lys Ala Leu Ala Pro Val Gly Ile Arg Glu Val Asn Phe Val Phe
            340                 345                 350

Gln Val Asp Gly Asp Arg Leu Lys Gln Arg Ile Lys His Ser Leu Gln
        355                 360                 365

Tyr Pro Lys Ser Cys Ala Asp Leu Arg Asn Glu Arg
    370                 375                 380

<210> SEQ ID NO 3
<211> LENGTH: 1275
<212> TYPE: DNA
<213> ORGANISM: Penicillium multicolor
```

<400> SEQUENCE: 3

```
atggcaccta agaaaatcat cattgacact gacccgggta tcgatgacat cctggcactg      60
ctgctggctc tgtcatctaa gccagaggat gttgagattc tacttatctc tttaacattt     120
ggaaacattg aggtgaagaa ctgtcttcga aatgtggtct ccatgtttca tatcctcgag     180
cgcgagatcc agtggcgtcg tggtaacggc aagtccgaag gctatggcac tatgcgtgct     240
ttccgcccag tagtagccgt gggagcgaaa gatcccttgg aagaccagaa gatgctcgct     300
gattatttcc atggaaccga tggccttggt ggcatccatg ctagtcaccc acatctcact     360
ccaagcaagg cctgggagca tctattcacc ccggccgtgg atccccaggg gatcgagcct     420
gtgcaaacgg gagctggtcc cggcgaccat tcctttatcc catcaagact acctgcacac     480
aaggagattc ttcgtgcact cgccagaat gagcctgaca ccgtgactct cgtggcggtt      540
ggtccactga ccaacttggc cttggcagca gcagaggatc ccgaaacctt cctacgtgtc     600
aaggaggtcg ttgtgatggg tggagcaatc aaccagcctg aaatgtcac ccccgttgga      660
gaattcaacg cctacgcaga cgccgttgca gctgcgcgag tctttgcgct gacatcacct     720
aatcccaact cgactctacc accgaccacg agtccactac ttggcctgta ccctgcaaag     780
ctcagccgac aattgactct gcgtctcttc ccgctggaca tcaccctgcg ccataacctg     840
tcccgcggcc aattccgcca agcagttgag cctctcctcg caacaggctc accctcgct     900
gaatgggtga cagcattcat gggacacacg ttccgaaccc tggaacgcct gcaccccggc     960
catgagggcg atgaagccca gctgagtctc cacgaccctg tctgtgtgtg gtatgccctt    1020
acagcagagg attcgcactg gactcctcc gccaattccc cagaggacat tcgtgttgag     1080
acattgggcc agtggacgcg tggtatgtgc gtaatcgatg ccgaaaccg ccataagatt    1140
gatggcgacg aggaaagctc gagtgatcat ggtctgtggt tgagtgctcg tgcaggaaac    1200
cgcattttgc gaatggatgg atcgccagcc gaacacacgt tcggcaagat cctcatcgat    1260
agaatcttcc actaa                                                     1275
```

<210> SEQ ID NO 4
<211> LENGTH: 1016
<212> TYPE: DNA
<213> ORGANISM: Penicillium multicolor

<400> SEQUENCE: 4

```
gtacccattt tctaacacta tctggacagc acccacatct cactccaagc aaggcctggg      60
agcatctatt caccccggcc gtggatcccc aggggatcga gcctgtgcaa acggagctg      120
gtcccggcga ccattccttt atcccatcaa gactacctgc acacaaggag attcttcgtg     180
cactgcgcca gaatgagcct gacaccgtga ctctcgtggc ggttggtcca ctgaccaact     240
tggccttggc agcagcagag gatcccgaaa ccttcctacg tgtcaaggag gtcgttgtga     300
tgggtggagc aatcaaccag cctggaaatg tatgaacccc gtcgaaacac ccatttgata     360
ataagtcatt aaccgcgatt gactaggtca ccccgttgg agaattcaac gcctacgcag      420
acgccgttgc agctgcgcga gtctttgcgc tgacatcacc taatcccaac tcgactctac     480
caccgaccac gagtccacta cttggcctgt accctgcaaa gctcagccga caattgactc     540
tgcgtctctt cccgctggac atcaccctgc gccataacct gtcccgcggc caattccgcc     600
aagcagttga gcctctcctc gcaacaggct caccctcgc tgaatgggtg acagcattca      660
tgggacacac gttccgaacc ctggaacgcc tgcaccccgg ccatgagggc gatgaagccc     720
agctgagtct ccacgaccct gtctgtgtgt ggtatgccct tacagcagag gattcgcact     780
```

```
ggactccctc cgccaattcc ccagaggaca ttcgtgttga cattgggc cagtggacgc     840 gtggtatgtg cgtaatcgat ggccgaaacc gccataagat tgatggcgac gaggaaagct    900
cgagtgatca tggtctgtgg ttgagtgctc gtgcaggaaa ccgcattttg cgaatggatg    960
gatcgccagc cgaacacacg ttcggcaaga tcctcatcga tagaatcttc cactaa      1016

<210> SEQ ID NO 5
<211> LENGTH: 1143
<212> TYPE: DNA
<213> ORGANISM: Penicillium multicolor

<400> SEQUENCE: 5
atgcatttcc ctgtttcatt gccgctgttg tgcggctctt tgctgcctct catcaccggc     60
accctggcag tgcccaaggc ctcgcgtgcc gacaagcact atgccatcat ggacaatgat    120
tggtacacag cgggtttcgt gccttacctg atcgccctcg atgcgatgt ggaggttctg    180 ggcctagcct ctgacaccgc aaacacctgg cagcctcagg tcgctctgca cgctgtcgca    240
actctggaag ctggcaactt gagctgtatc cccgtttacc caggctcgac atggccgctc    300
atcaacaccc caaccgcttc caggcgtgg gaaatggttc atggcaagct gccatgggag    360
ggtgcttttg cgccggagaa caagactctc gaggccgagg gtaacgatcc tacctctggc    420
aaccccaacc gtatcgtcaa ggccgctttc aaggaagggt tccccaaggg caagcccgag    480
aacagaacat ctgctgccaa cttcatggtc gagatggtgc acaagtaccc cggccaggtc    540
tcgatctact ctgctggagc cctgaccaat gttgcgctgg ctgtgcgcat ggatccccag    600
tttgcatctc tggctaagga gttggttatc atgggtggat acgtcgattt gaatatgctc    660
caggccactg gaagtgtctt gctggctgat cttcaatctg atatcaactt gatgattgat    720
cccgaggcct ccaagatcgc attgactgcc gaattcccca atatcaccat cgccggtaac    780
gtcgccaacc aggtctttcc taccaaggag ttcgtcgacg gatcgcctc cgttccaaac    840 ccctacagca agctcttcca cgactactac gatctgtcct tcccttctg ggatgagacg    900 gctgccgcgc tgatggttga ccctactctt gctaccaacc agacctctgt cttcctcgac    960
gtggataccg cttatggtag ccccaactat ggtaacattc acgtttacca gaaggctctt   1020 gccctgttg gtatccggga ggtcaacttt gtcttccagg ttgatgggga tagacttaag   1080
cagcgcatca agcactctct gcagtacccc aagtcatgcg ccgacctgag aaatgagcgt   1140
tga                                                                 1143

<210> SEQ ID NO 6
<211> LENGTH: 847
<212> TYPE: DNA
<213> ORGANISM: Penicillium multicolor

<400> SEQUENCE: 6
acgatcctac tctggcaac cccaaccgta tcgtcaaggc cgctttcaag gaagggttcc     60
ccaagggcaa gcccgagaac agaacatctg ctgccaactt catggtcgag atggtgcaca    120
agtaccccgg ccaggtctcg atctactctg ctggagccct gaccaatgtt gcgctggctg    180
tgcgcatgga tccccagttt gcatctctgg ctaaggagtt ggttatcatg ggtggatacg    240
tcgatttgaa tatgctccag gccactggaa gtgtcttgct ggctgatctt caatctgatg    300
tatgtttcat tccggcttc tatcagctgt gttcatctgc taacttctct ttagatcaac    360
ttgatgattg atcccgaggc ctccaagatc gcattgactg ccgaattccc caatatcacc    420
```

-continued

```
atcgccggta acgtcgccaa ccaggtctttt cctaccaagg agttcgtcga cgagatcgcc    480
tccgttccaa accccctacag caagctcttc cacgactact acgatctgtc cttccccttc    540
tgggatgaga cggctgccgc gctgatggtt gaccctactc ttgctaccaa ccagacctct    600
ggtgagttta atctcgcatt gacacttgta tgaacaaatc taacagctta tagtcttcct    660
cgacgtggat accgcttatg gtagccccaa ctatggtaac attcacgttt accagaacgc    720
tcttgcccct gttggtatcc gggaggtcaa ctttgtcttc caggttgatg gggatagact    780
taagcagcgc atcaagcact ctctgcagta ccccaagtca tgcgccgacc tgagaaatga    840
gcgttga                                                               847
```

<210> SEQ ID NO 7
<211> LENGTH: 15
<212> TYPE: PRT
<213> ORGANISM: Penicillium multicolor

<400> SEQUENCE: 7

Ala Asp Lys His Tyr Ala Ile Met Asp Asn Asp Trp Tyr Thr Ala
1               5                   10                  15

<210> SEQ ID NO 8
<211> LENGTH: 15
<212> TYPE: PRT
<213> ORGANISM: Penicillium multicolor

<400> SEQUENCE: 8

Ala Asp Lys His Tyr Ala Ile Met Asp Asn Asp Trp Tyr Thr Ala
1               5                   10                  15

<210> SEQ ID NO 9
<211> LENGTH: 9
<212> TYPE: PRT
<213> ORGANISM: Penicillium multicolor

<400> SEQUENCE: 9

Val Glu Thr Lys Leu Ile Phe Leu Thr
1               5

<210> SEQ ID NO 10
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: inosine
<220> FEATURE:
<221> NAME/KEY: misc_feature
<222> LOCATION: (6)..(6)
<223> OTHER INFORMATION: g or a
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (10)..(10)
<223> OTHER INFORMATION: a or c
<220> FEATURE:
<221> NAME/KEY: misc_feature
<222> LOCATION: (12)..(12)
<223> OTHER INFORMATION: any of a, g, c, or t
<220> FEATURE:
<221> NAME/KEY: misc_feature
<222> LOCATION: (15)..(15)

```
<223> OTHER INFORMATION: t or c
<220> FEATURE:
<221> NAME/KEY: misc_feature
<222> LOCATION: (16)..(16)
<223> OTHER INFORMATION: t or c
<220> FEATURE:
<221> NAME/KEY: misc_feature
<222> LOCATION: (18)..(18)
<223> OTHER INFORMATION: inosine

<400> SEQUENCE: 10
acnaartaym gnttyytnac                                            20

<210> SEQ ID NO 11
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (4)..(4)
<223> OTHER INFORMATION: any of a, g, c, or t
<220> FEATURE:
<221> NAME/KEY: misc_feature
<222> LOCATION: (7)..(7)
<223> OTHER INFORMATION: any of a, g, c, or t
<220> FEATURE:
<221> NAME/KEY: misc_feature
<222> LOCATION: (9)..(9)
<223> OTHER INFORMATION: g or t
<220> FEATURE:
<221> NAME/KEY: misc_feature
<222> LOCATION: (10)..(10)
<223> OTHER INFORMATION: any of a, g, c, or t
<220> FEATURE:
<221> NAME/KEY: misc_feature
<222> LOCATION: (16)..(16)
<223> OTHER INFORMATION: t or c
<220> FEATURE:
<221> NAME/KEY: misc_feature
<222> LOCATION: (19)..(19)
<223> OTHER INFORMATION: any of a, g, c, or t

<400> SEQUENCE: 11
catnccnckn gtccaytgnc c                                          21

<210> SEQ ID NO 12
<211> LENGTH: 26
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: a, c, or t
<220> FEATURE:
<221> NAME/KEY: misc_feature
<222> LOCATION: (12)..(12)
<223> OTHER INFORMATION: t or c
<220> FEATURE:
<221> NAME/KEY: misc_feature
<222> LOCATION: (15)..(15)
<223> OTHER INFORMATION: t or c
<220> FEATURE:
<221> NAME/KEY: misc_feature
<222> LOCATION: (18)..(18)
<223> OTHER INFORMATION: t or c
<220> FEATURE:
<221> NAME/KEY: misc_feature
```

```
<222> LOCATION: (24)..(24)
<223> OTHER INFORMATION: t or c

<400> SEQUENCE: 12
gcnathatgg ayaaygaytg gtayac                                         26

<210> SEQ ID NO 13
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (3)..(3)
<223> OTHER INFORMATION: any of a, g, c, or t
<220> FEATURE:
<221> NAME/KEY: misc_feature
<222> LOCATION: (6)..(6)
<223> OTHER INFORMATION: any of a, g, c, or t
<220> FEATURE:
<221> NAME/KEY: misc_feature
<222> LOCATION: (9)..(9)
<223> OTHER INFORMATION: t or c
<220> FEATURE:
<221> NAME/KEY: misc_feature
<222> LOCATION: (12)..(12)
<223> OTHER INFORMATION: g or a
<220> FEATURE:
<221> NAME/KEY: misc_feature
<222> LOCATION: (18)..(18)
<223> OTHER INFORMATION: g or a
<220> FEATURE:
<221> NAME/KEY: misc_feature
<222> LOCATION: (21)..(21)
<223> OTHER INFORMATION: any of a, g, c, or t

<400> SEQUENCE: 13
gcngcngtyt crtcccaraa ngg                                            23

<210> SEQ ID NO 14
<211> LENGTH: 25
<212> TYPE: DNA
<213> ORGANISM: Artificial Sequence
<220> FEATURE:
<223> OTHER INFORMATION: primer

<400> SEQUENCE: 14
atggcaccta agaaaatcat cattg                                          25

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ttagtggaag attctatcga tgagg                                          25

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
atgcatttcc ctgtttcatt gccgc                                          25
```

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17

```
tcaacgctca tttctcaggt cgg                                          23
```

<210> SEQ ID NO 18
<211> LENGTH: 574
<212> TYPE: DNA
<213> ORGANISM: Artificial Sequence
<220> FEATURE:
<223> OTHER INFORMATION: probe

<400> SEQUENCE: 18

```
gaggatcccg aaaccttcct acgtgtcaag gaggtcgttg tgatgggtgg agcaatcaac   60
cagcctggaa atgtatgaac cccgtcgaaa cacccatttg ataataagtc attaaccgcg  120
attgactagg tcaccccgt tggagaattc aacgcctacg cagacgccgt tgcagctgcg   180
cgagtctttg cgctgacatc acctaatccc aactcgactc taccaccgac cacgagtcca  240
ctacttggcc tgtaccctgc aaagctcagc cgacaattga ctctgcgtct cttcccgctg  300
gacatcaccc tgcgccataa cctgtcccgc ggccaattcc gccaagcagt tgagcctctc  360
ctcgcaacag gctcacccct cgctgaatgg gtgacagcat tcatgggaca cacgttccga  420
accctggaac gcctgcaccc cggccatgag ggcgatgaag cccagctgag tctccacgac  480
cctgtctgtg tgtggtatgc ccttacagca gaggattcgc actggactcc ctccgccaat  540
tccccagagg acattcgtgt tgagacattg ggcc                              574
```

<210> SEQ ID NO 19
<211> LENGTH: 509
<212> TYPE: DNA
<213> ORGANISM: Artificial Sequence
<220> FEATURE:
<223> OTHER INFORMATION: probe

<400> SEQUENCE: 19

```
agacaccgca aacacctggc agcctcaggt cgctctgcac gctgtcgcaa ctctggaagc   60
tggcaacttg agctgtatcc ccgtttaccc aggctcgaca tggccgctca tcaacacccc  120
caaccgcttc caggcgtggg aaatggttca tggcaagctg ccatgggagg gtgcttttgc  180
gccggagaac aagactctcg aggccgaggg taacgatcct acctctggca accccaaccg  240
tatcgtcaag gccgctttca aggaagggtt ccccaagggc aagcccgaga acagaacatc  300
tgctgccaac ttcatggtcg agatggtgca caagtacccc ggccaggtct cgatctactc  360
tgctggagcc ctgaccaatg ttgcgctggc tgtgcgcatg gatccccagt ttgcatctct  420
ggctaaggag ttggttatca tgggtggata cgtcgatttg aatatgctcc aggccactgg  480
aagtgtcttg ctggctgatc ttcaatctg                                   509
```

METHOD FOR PRODUCING NUCLEIC ACID SEASONING

TECHNICAL FIELD

The present invention relates to a nucleic acid-based seasoning. More specifically, the invention relates to a method for producing a nucleic acid-based seasoning such as a yeast extract. The present application claims priority based on Japanese Patent Application No. 2016-199543 filed on Oct. 7, 2016, the entire contents of which are incorporated herein by reference.

BACKGROUND ART

Nucleic acid-based seasonings typified by yeast extracts are used in various foods and the like for imparting or enhancing umami (delicious taste) and rich taste. Yeast extracts are roughly classified into those of high amino acid type rich in amino acids and those of high nucleic acid type having a high nucleic acid content. The main taste components in the latter yeast extracts are 5'-guanylic acid (GMP) and 5'-inosinic acid (IMP). Various studies focusing on these taste components have been made in order to enhance their effect (see, for example, PTL 1 to PTL 3).

CITATION LIST

Patent Literatures

[PTL 1] JP H06-113789 A
[PTL 2] WO 2015/141531
[PTL 3] WO 2003/055333

SUMMARY OF INVENTION

Technical Problem

In light of the current situation where nucleic acid-based seasonings are used in a wide range of foods and beverages and the consumers' desire for more delicious foods and new flavors, it is desired to further enhance the taste of nucleic acid-based seasonings. In order to respond to such a demand, it is an object of the present invention to provide a nucleic acid-based seasoning improved in taste.

Solution to Problem

GMP, one of the taste components of yeast extracts of high nucleic acid type, is produced by causing a nuclease to act on nucleic acids in yeast. Therefore, the amount of GMP in the yeast extracts depends on the amount of nucleic acids originally contained in the raw material yeast, and its content is naturally limited even if the production efficiency is enhanced, for example, by optimizing the acting conditions of the enzyme. On the other hand, IMP is produced by converting 5'-adenylic acid (AMP) produced by nuclease treatment with an AMP-deaminase. Therefore, like GMP, the content of IMP also depends on the raw material yeast. Therefore, the present inventors have made further studies from a viewpoint different from conventional ones. Specifically, the inventors, focusing on the nucleotide produced in the process of producing a yeast extract, have studied whether the incorporation of a process of treatment with a nucleosidase as an enzyme potentially capable of acting using the nucleotide as a substrate could make it possible to enhance the taste and to impart a new taste. As a result of studies, it has been surprisingly found that nucleosidase treatment is effective for improving or enhancing the taste. From the expectation that the amounts of the taste substances GMP and IMP will be decreased by the action of the nucleosidase, in addition to the fact that purine bases (adenine, guanine, hypoxanthine, etc.) which are reaction products of the nucleosidase have not been recognized as taste substances, this result can be said to be quite unexpected.

The following inventions are mainly based on the above results and analysis thereon.

[1] A method for producing a nucleic acid-based seasoning, comprising a step of treating a ribonucleotide-containing material with a nucleosidase.

[2] The production method according to [1], wherein the ribonucleotide-containing material is a ribonuclease-treated ribonucleic acid-containing material.

[3] The production method according to [2], comprising the following steps (1) and (2):
(1) providing a ribonucleotide-containing material obtained by treating a ribonucleic acid-containing material with a ribonuclease; and
(2) treating the ribonucleotide-containing material with an AMP-deaminase and a nucleosidase separately or simultaneously.

[4] The production method according to [3], wherein step (2) comprises the following steps (2-1) and (2-2):
(2-1) treating the ribonucleotide-containing material with an AMP-deaminase, and
(2-2) treating the treated product after step (2-1) with a nucleosidase.

[5] The production method according to [1], wherein the ribonucleotide-containing material is a ribonucleic acid-containing material treated with a ribonuclease and an AMP-deaminase.

[6] The production method according to any one of [1] to [5], wherein the ribonucleotide-containing material comprises purine nucleotides.

[7] The production method according to any one of [1] to [6], wherein the ribonucleic acid-containing material is a yeast lysate.

[8] The production method according to any one of [1] to [7], wherein the nucleosidase comprises the amino acid sequence of SEQ ID NO: 1 or an amino acid sequence having 85% or more identity with the amino acid sequence, or the amino acid sequence of SEQ ID NO: 2 or an amino acid sequence having 88% or more identity with the amino acid sequence.

[9] The production method according to [8], wherein the amino acid sequence of the nucleosidase is an amino acid sequence having 90% or more identity with the amino acid sequence of SEQ ID NO: 1 or the amino acid sequence of SEQ ID NO: 2.

[10] The production method according to any one of [1] to [7], wherein the nucleosidase has the following enzymological properties:
(1) action: catalyzing a reaction of hydrolyzing purine nucleosides into D-ribose and purine bases;
(2) molecular weight: about 49 kDa (by SDS-PAGE) when the nucleosidase does not contain N-linked oligosaccharides;
(3) optimum temperature: 55° C. to 60° C.; and
(4) thermal stability: stable at 55° C. or lower (pH 6.0, for 30 minutes).

[11] The production method according to claim 10, wherein the nucleosidase further has the following enzymological properties:

(5) optimum pH: 3.5; and (6) pH stability: stable in the range of pH 3.5 to 7.5 (30° C., for 30 minutes).

[12] The production method according to any one of [1] to [7], wherein the nucleosidase has the following enzymological properties:

(1) action: catalyzing a reaction of hydrolyzing purine nucleosides into D-ribose and purine bases;

(2) molecular weight: about 40 kDa (by SDS-PAGE) when the nucleosidase does not contain N-linked oligosaccharides;

(3) optimum temperature: 50° C. to 55° C.; and (4) thermal stability: stable at 65° C. or lower (pH 4.5, for 60 minutes).

[13] The production method according to [12], wherein the nucleosidase further has the following enzymological properties:

(5) optimum pH: 4.5; and (6) pH stability: stable in the range of pH 3.5 to 7.5 (30° C., for 30 minutes).

[14] The production method according to any one of [8] to [13], wherein the nucleosidase is derived from *Penicillium multicolor*.

[15] The production method according to [14], wherein the *Penicillium multicolor* is an IFO 7569 strain or a mutant strain thereof.

[16] A nucleic acid-based seasoning obtained by the production method according to any one of [1] to [15].

[17] The nucleic acid-based seasoning according to [16], wherein the purine base content is increased by the action of the nucleosidase.

BRIEF DESCRIPTION OF DRAWINGS

FIG. 5 Molecular weight of each purified enzyme (peaks 1 to 3). This figure also shows the results of N-terminal amino acid analysis.

FIG. 6 Probe sequences used for gene cloning. Upper: probe sequence for PN1 (SEQ ID NO: 18) and Lower: probe sequence for PN2 (SEQ ID NO: 19).

FIG. 7 Results of gene cloning. This figure shows a genomic sequence (upper, SEQ ID NO: 4) encoding the enzyme (PN1) of peak 3 and a genomic sequence (lower, SEQ ID NO: 6) encoding the enzyme (PN2) of peaks 1 and 2.

FIG. 8 Results of gene cloning. This figure shows a cDNA sequence (upper, SEQ ID NO: 3) encoding the enzyme (PN1) of peak 3 and a cDNA sequence (lower, SEQ ID NO: 5) encoding the enzyme (PN2) of peaks 1 and 2.

FIG. 9 Results of gene cloning. This figure shows the amino acid sequence of the enzyme (PN1) of peak 3 (upper, SEQ ID NO: 1) and the amino acid sequence of enzyme (PN2) of peaks 1 and 2 (lower, SEQ ID NO: 2).

FIG. 10 Results of gene cloning. The enzyme (PN1) of peak 3 and enzyme (PN2) of peaks 1 and 2 were compared in terms of the number of cDNA bases, number of introns, amino acid length, molecular weight, and estimated pI.

FIG. 20 Result of sensory evaluation.

DESCRIPTION OF EMBODIMENTS

Figure 1:
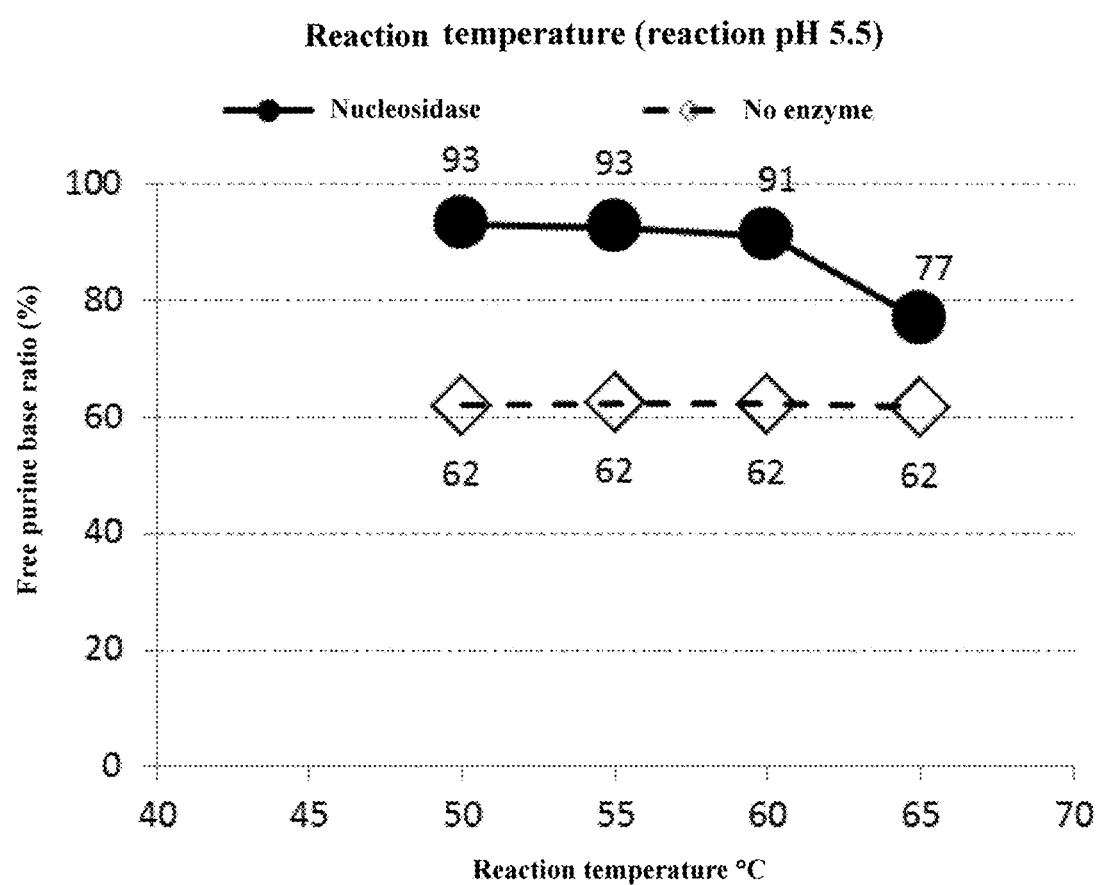
FIG. 1 Operative temperature range of a nucleosidase derived from a *Penicillium multicolor* IFO 7569 strain. An enzymatic reaction was carried out under each temperature condition in the presence of seven kinds of purine bodies, and the free purine base ratio was determined.

1. Method for Producing Nucleic Acid-Based Seasoning

A first aspect of the present invention relates to a method for producing a nucleic acid-based seasoning. The nucleic acid-based seasoning means a composition comprising a nucleic acid and/or a nucleotide as a taste component and used for seasoning. The seasoning referred to herein includes adjustment, change, and enhancement of taste. The raw material for the nucleic acid-based seasoning is not particularly limited as long as it contains a ribonucleic acid and/or a ribonucleotide, and there are preferably used natural products abundantly containing a ribonucleic acid such as yeast, eggs (for example, fish eggs), milt of fish (for example, salmon or blowfish), fish and shellfish, and soybean, or processed products thereof. Ribonucleic acids are polymers in which ribonucleotides are linked by phosphodiester bonds. A ribonucleotide as a constituent of ribonucleic acids is a substance composed of a phosphate group, D-ribose, and a nucleic acid base (purine base or pyrimidine base). Those having a purine base are referred to as purine nucleotides, and those having a pyrimidine base are referred to as pyrimidine nucleotides. Examples of the purine nucleotides include 5'-adenylic acid (AMP), 5'-guanylic acid (GMP), 5'-inosinic acid (IMP), 5'-xanthylic acid (XMP), and the like. Examples of the pyrimidine nucleotides include 5'-cytidic acid (CMP), 5'-uridic acid (UMP), and the like. The taste component or taste substance is a substance which causes a taste.

In the production method of the present invention, a step of treating a ribonucleotide-containing material with a nucleosidase is carried out. The ribonucleotide-containing material is not particularly limited as long as it contains a ribonucleotide. It may contain a ribonucleotide alone or may contain a ribonucleic acid, a deoxyribonucleic acid, a deoxyribonucleotide, or the like, in addition to a ribonucleotide.

The ribonucleotide to be contained is preferably a purine nucleotide. Also, it is preferable that the ribonucleotide-containing material contain taste purine nucleotides GMP and/or IMP. The ribonucleotide-containing material is obtained, for example, by acid/alkali decomposition or enzymatic decomposition of a ribonucleic acid-containing material. Preferably, the ribonucleotide-containing material is obtained by treating a ribonucleic acid-containing material with an enzyme such as a ribonuclease or an AMP-deaminase. Examples of preferred ribonucleic acid-containing materials can include a yeast lysate.

In the present invention, treatment with a nucleosidase is carried out based on the surprising finding that the taste was improved or enhanced by incorporating a nucleosidase treatment process in the process of producing a yeast extract. Nucleosidases are used to produce purine bases. Various nucleosidases can be used as long as they exhibit an action of producing purine bases using purine nucleotides as substrates. Preferably, this step is carried out using the novel nucleosidase which will be described below. The nucleosidase has been confirmed to have an action of producing purine bases using purine nucleotides as substrates. As mentioned in the past reports, it has been found that several nucleosidases (specifically, nucleosidase derived from *Ochrobactrum anthropi* used in the experiments described in the article Appl. Environ. Microbiol. 67, 1783-1787 (2001), nucleosidase derived from *Aspergillus niger* used in the experiments described in the article Can. J. Biochem. 56, 345-348 (1978), etc.) have the above action.

As the ribonucleotide-containing material, a ribonucleic acid-containing material treated with a ribonuclease or a ribonucleic acid-containing material treated with a ribonuclease and an AMP-deaminase can be used. In the former case, for example, the following steps (1) and (2) are carried out:

(1) providing a ribonucleotide-containing material obtained by treating a ribonucleic acid-containing material with a ribonuclease; and (2) treating the ribonucleotide-containing material with an AMP-deaminase and a nucleosidase separately or simultaneously.

In step (1), a ribonucleotide-containing material obtained by treating a ribonucleic acid-containing material with a ribonuclease is provided, but it is also possible to acquire a ribonucleic acid-containing material treated with a ribonuclease in advance and use it as the ribonucleotide-containing material to be used in this step, or to treat a ribonucleic acid-containing material with a ribonuclease when implementing the present invention.

As the ribonucleic acid-containing material, a yeast lysate is preferably used. In this preferred embodiment, a yeast extract as a nucleic acid-based seasoning is produced using yeast as a raw material. The raw material yeast is not particularly limited unless it is not suitable for use in foods. For example, there can be employed yeasts used in the food industry, including yeast of the genus *Saccharomyces* such as *Saccharomyces cerevisiae* or *Saccharomyces pastorianus*; yeast of the genus *Candida* such as *Candida utilis*; yeast of the genus *Kluyveromyces* such as *Kluyveromyces lactis* or *Kluyveromyces marxianus*; yeast of the genus *Pichia* such as *Pichia pastoris*; yeast of the genus *Debaryomyces* such as *Debaryomyces hansenii*; and yeast of the genus *Zygosaccharomyces* such as *Zygosaccharomyces mellis*. Also, it is possible to use a yeast collected after brewing beer, sake, or the like. It is also possible to use a yeast subjected to drying treatment (dried yeast) after collection.

A yeast lysate can be prepared by lysing a yeast. For example, the yeast after culture can be crushed or lysed by an enzymatic decomposition method, a self-digestion method, an alkaline extraction method, a hot water extraction method, an acid decomposition method, an ultrasonic crushing method, crushing with a homogenizer, a freezing-thawing method, or the like (two or more thereof may be used in combination), whereby a yeast lysate can be obtained. Yeast may be cultured by a conventional method.

In one preferred embodiment, the yeast after culture is heat-treated and then treated with a lytic enzyme to obtain an enzyme lysate. The conditions for the heat treatment can be, for example, 80° C. to 90° C. for 5 minutes to 30 minutes. As the lytic enzyme used for the enzymatic decomposition method, various enzymes can be used as long as they can lyse the cell wall of yeast. Specific examples of the lytic enzyme can include YL-T "Amano" L (Amano Enzyme Inc.). The reaction conditions may be set so as to be optimum or suitable for the lytic enzyme to be used, and specific examples thereof can include a temperature of 50 to 60° C. and a pH of 7.0 to 8.0. The reaction time is also not particularly limited, and can be, for example, 3 hours to 5 hours.

By treating the ribonucleic acid-containing material with a ribonuclease, the ribonucleic acids in the ribonucleic acid-containing material are decomposed, so that nucleotides such as GMP, which are taste substances, are produced. The ribonuclease to be used is not particularly limited, and Enzyme RP-1G (Amano Enzyme Inc.), nuclease "Amano" G (Amano Enzyme Inc.), and the like can be used. The reaction conditions may be set so as to be optimal or suitable for the ribonuclease to be used, and specific examples thereof can include a temperature of 65 to 70° C. and a pH of 5.0 to 5.5. The reaction time is also not particularly limited, and can be, for example, 3 hours to 16 hours.

The ribonucleotide-containing material provided in step (1) is subjected to treatment with an AMP-deaminase and treatment with a nucleosidase (step (2)). Before step (2), there may be removed part or all of unnecessary components, for example, cell bodies (e.g., yeast cell wall) when a yeast lysate is used as the ribonucleic acid-containing material. For removal of insoluble components, for example, a solid-liquid separation method, centrifugation treatment, sedimentation, filtration, decantation, compression, and the like can be used.

The AMP-deaminase is used to convert AMP produced by the ribonuclease treatment to IMP. In other words, taste IMP is produced by AMP-deaminase treatment. On the other hand, purine bases (adenine, guanine, xanthine, hypoxanthine, etc.) are produced from purine nucleotides by nucleosidase treatment.

The AMP-deaminase is an enzyme that hydrolyzes AMP to produce IMP and ammonia. The AMP-deaminase to be used is not particularly limited, and Deamizyme G (Amano Enzyme Inc.) or the like can be used.

The treatment with an AMP-deaminase and the treatment with a nucleosidase are carried out separately or simultaneously. That is, in one embodiment (the first embodiment), the treatment with one enzyme is performed, and then the treatment with the other enzyme is performed. In another embodiment (the second embodiment), these two enzymes are caused to act simultaneously. In the case of the first embodiment, preferably, the AMP deaminase treatment is followed by the nucleosidase treatment. That is, the following steps (2-1) and (2-2) are carried out in this order:

(2-1) treating the ribonucleotide-containing material with an AMP-deaminase, and (2-2) treating the treated product after step (2-1) with a nucleosidase.

In this way, it is possible to avoid a decrease in AMP (substrate of the AMP-deaminase) before the AMP-deaminase treatment, and the enzymatic reaction of the AMP-deaminase, i.e., the conversion of AMP to IMP, progresses in the state where the substrate is abundantly present. As a result, a nucleic acid-based seasoning having a high IMP content can be produced.

In the case of the first embodiment, the conditions for each enzyme reaction may be set so as to be optimum or suitable for the enzyme to be used. The reaction conditions are, for example, a temperature of 50 to 55° C. and a pH of 5.0 to 6.0 for the AMP-deaminase treatment, and a temperature of 50 to 60° C. and a pH of 4.5 to 5.5 for the nucleosidase treatment. The reaction time is also not particularly limited. For example, the time for the AMP-deaminase treatment is set to 3 hours to 5 hours, and the time for the nucleosidase treatment is set to 1 hour to 3 hours.

The second embodiment in which the AMP-deaminase and the nucleosidase are caused to act simultaneously can be said to be advantageous particularly in simplicity of operation. The reaction conditions in this embodiment are not particularly limited as long as both the enzymes can act. Examples of the reaction conditions can include a temperature of 50 to 55° C. and a pH of 5.0 to 6.0. An example of the reaction time is 1 hour to 5 hours.

The product obtained in step (2) can be applied as it is to various uses as a nucleic acid-based seasoning (for example, a yeast extract), but a purification process (for example, filtration or centrifugation), a concentration process (for example, evaporation concentration, freeze concentration, or membrane concentration), a drying process (for example, freeze drying or spray drying), or the like may be additionally carried out.

Also in the case where a ribonucleic acid-containing material subjected to ribonuclease treatment and AMP-deaminase treatment is used as the ribonucleotide-containing material, it is possible to acquire a ribonucleic acid-containing material treated with a ribonuclease and an AMP-deaminase in advance and use it as the ribonucleotide-containing material to be used in this step, or to treat a ribonucleic acid-containing material with a ribonuclease and an AMP-deaminase when the present invention is implemented, similarly to in the above case (in the case of using a ribonucleic acid-containing material treated with a ribonuclease as the ribonucleotide-containing material).

According to the production method of the present invention, it is possible to obtain a liquid or solid (typically powdery, granular, etc.) nucleic acid-based seasoning. The nucleic acid-based seasoning obtained by the production method of the present invention can be used for enhancing and adjusting the taste of various foods and beverages. Examples of applicable foods and beverages include processed marine products (chikuwa (tube-shaped fish paste cake), kamaboko (boiled fish paste), hanpen (pounded fish cake), sakiika (shredded and dried squid), dried fish, shiokara (salted fish guts), fish sausage, tsukudani (preservable food boiled down in soy sauce), canned products, etc.); processed meat products (ham, bacon, sausage, jerky, corned beef, restructured meat, etc.); processed vegetable products (pickles, daily dishes, etc.); breads (breads, sweet buns, etc.); confectionery (snacks, bean confectionery, rice crackers, frozen desserts, etc.); seasonings (dipping sauce, broth, dressing, sauce, etc.); soups; roux (curry roux, stew roux, etc.); dairy products; carbonated drinks; non-alcoholic drinks; milk drinks; coffee drinks; fruit drinks; and tea-based beverages.

Here, typical taste substances in nucleic acid-based seasonings are GMP and IMP. Also in the nucleic acid-based seasoning obtained by the production method of the present invention, these two taste substances are important in defining the taste, but, in light of the experimental results presented in the Examples which will be described later, substances other than these substances (specifically, purine bases) also contribute to the overall taste. The nucleic acid-based seasoning obtained by the production method of the present invention is characteristic in this respect, and is different from those obtained by conventional production methods in terms of the components constituting the taste.

2. Nucleosidase and Producer Bacterium for the Nucleosidase

The second aspect of the present invention provides a nucleosidase and a producer bacterium for the nucleosidase. The present inventors have succeeded in acquiring two kinds of nucleosidases (hereinafter referred to as "PN1" and "PN2" corresponding to the indications in the Examples; in addition, these two nucleosidases are collectively referred to as "the present enzyme" in some cases) from *Penicillium multicolor*, and identified the gene sequences and amino acid sequences thereof. Based on the results, the present enzymes have a characteristic feature of including the amino acid sequence of SEQ ID NO: 1 or the amino acid sequence of SEQ ID NO: 2, or an amino acid sequence equivalent to either one of these amino acid sequences. The amino acid sequence of SEQ ID NO: 1 corresponds to PN1, and the amino acid sequence of SEQ ID NO: 2 corresponds to PN2.

The term "equivalent amino acid sequence" in this case means an amino acid sequence which is partially different from the reference amino acid sequence (i.e. the amino acid sequence of SEQ ID NO:1 or the amino acid sequence of SEQ ID NO:2), but the difference does not substantially influence the function of the protein (nucleosidase activity). Thus, an enzyme having a polypeptide chain of the equivalent amino acid sequence shows a nucleosidase activity. The degree of the activity is not particularly limited as long as the function of a nucleosidase can be exhibited, but is preferably equivalent to or higher than that of the enzyme having a polypeptide chain of the reference sequence.

The term "partial difference in the amino acid sequence" typically means mutation (change) in the amino acid sequence caused by deletion or substitution of one to several (up to, for example, 3, 5, 7, or 10) amino acids composing the amino acid sequence, or addition, insertion, or combination thereof of one to several (up to, for example, 3, 5, 7, or 10) amino acids. The difference in the amino acid sequence is acceptable as long as the nucleosidase activity is maintained (the activity may be varied to a degree). As long as the conditions are satisfied, the position of the difference in the amino acid sequence is not particularly limited, and the difference may arise in a plurality of positions. As to the amino acid sequence of SEQ ID NO:1, rhe term "plurality" means, for example, a number corresponding to less than about 15%, preferably less than about 10%, more preferably less than about 5%, even more preferably less than about 3% of the total amino acids, and most preferably less than about 1%. As to the amino acid sequence of SEQ ID NO:2, the term "plurality" means, for example, a number corresponding to less than about 12%, preferably less than about 10%, more preferably less than about 5%, even more preferably less than about 3% of the total amino acids, and most preferably less than about 1%. More specifically, in a case where the amino acid sequence of SEQ ID NO:1 is the reference amino acid sequence, the equivalent protein has, for example, about 85% or more, preferably about 90% or more, more preferably about 95% or more, much more preferably about 98% or more, and most preferably about 99% or more identity with the reference amino acid sequence, whereas in a case where the amino acid sequence of SEQ ID NO:2 is the reference amino acid sequence, the equivalent protein has, for example, about 88% or more, preferably about 90% or more, more preferably about 95% or more, much more preferably about 98% or more, and most preferably about 99% or more identity with the reference amino acid sequence. The difference of the amino acid sequence may arise in a plurality of positions. As to SEQ ID NO:1, it is preferable that histidine (H) at position 331, which is deduced to form the active center, and aspartic acid (D) at position 11, aspartic acid (D) at position 15, aspartic acid (D) at position 16 and aspartic acid (D) at position 332, which are deduced to be involved in catalysis, are not subjected to deletion or substitution.

Preferably, the equivalence protein is obtained by causing conservative amino acid substitution in an amino acid residue which is not essential for nucleosidase activity. The term "conservative amino acid substitution" means the substitution of an amino acid residue with another amino acid residue having a side chain with similar properties. Amino acid residues are classified into several families according to their side chains, such as basic side chains (for example, lysine, arginine, and histidine), acidic side chains (for example, aspartic acid and glutamic acid), uncharged polar side chains (for example, glycine, asparagine, glutamine, serine, threonine, tyrosine, and cysteine), nonpolar side chains (for example, alanine, valine, leucine, isoleucine, proline, phenylalanine, methionine, and tryptophan), β branched side chains (for example, threonine, valine, and isoleucine), and aromatic side chains (for example, tyrosine, phenylalanine, tryptophan, and histidine). Conservative amino acid substitution is preferably the substitution between amino acid residues in one family.

The identity (%) between two amino acid sequences or two nucleic acid sequences (hereinafter, the term "two sequences" are used for representing either of two sequences) can be determined by the following procedure. Firstly, two sequences are aligned for optimum comparison of the two sequences (for example, a gap may be introduced into the first sequence so as to optimize the alignment with respect to the second sequence). When a molecule (amino acid residue or nucleotide) at a specific position in the first sequence and a molecule in the corresponding position in the second sequence are the same as each other, the molecules in the positions are defined as being identical. The identity between two sequences is a function of the number of identical positions shared by the two sequences (i.e., identity (%)=number of identical positions/total number of positions×100). Preferably, the number and size of the gaps, which are required to optimize the alignment of the two sequences, are taken into consideration.

The comparison and determination of the identity between two sequences can be carried out by using a mathematical algorithm. A specific example of the mathematical algorithm that can be used for comparing the sequences includes an algorithm described in Karlin and Altschul (1990) Proc. Natl. Acad. Sci. USA 87:2264-68 and modified by Karlin and Altschul (1993) Proc. Natl. Acad. Sci. USA 90:5873-77. However, the algorithm is not necessarily limited to this. Such an algorithm is incorporated in NBLAST program and XBLAST program (version 2.0) described in Altschul et al. (1990) J. Mol. Biol. 215: 403-10. In order to obtain an equivalent nucleic acid sequence, for example, BLAST nucleotide search with score=100 and word length=12 may be carried out by the NBLAST program. In order to obtain an equivalent amino acid sequence, for example, BLAST polypeptide search with score=50 and word length=3 may be carried out by the XBLAST program. In order to obtain gapped alignments for comparison, Gapped BLAST described in Altschul et al., (1997) Amino Acids Research 25(17): 3389-3402 can be utilized. In using BLAST and Gapped BLAST, the default parameters of the corresponding programs (e.g., XBLAST and NBLAST) can be used. In detail, see http://www.ncbi.nlm.nih.gov. Another example of the mathematical algorithm that can be used for comparing sequences includes an algorithm described in Meyers and Miller (1988) Comput. Appl. Biosci. 4: 11-17. Such programs are incorporated into the ALIGN program that can be used for, for example, GENESTREAM network server (IGH Montpellier, France) or ISREC server. When the ALIGN program is used for comparison of the amino acid sequences, for example, PAM120 weight residue table can be used in which a gap length penalty is 12 and a gap penalty is 4.

The identity between two amino acid sequences can be determined by using the GAP program in the GCG software package, using Blossom 62 matrix or PAM250 matrix with the gap weight of 12, 10, 8, 6, or 4, and the gap length weight of 2, 3, or 4. The identity between two nucleic acid sequences can be determined by using the GAP program in the GCG software package (available at http://www.gcg.com), with the gap weight of 50, and the gap length weight of 3.

The present enzyme may be a portion of a larger protein (for example, a fused protein). Examples of the sequence added to a fused protein include the sequences useful for purification of multiple histidine residues, and addition sequences which ensures stability in recombination production.

The present enzyme having the above-described amino acid sequence is readily prepared by a genetic engineering technique. For example, an appropriate host cell (for example, *Escherichia coli*) is transformed by a DNA encoding the present enzyme, and the protein expressed in the transformant is collected, and thereby preparing the present enzyme. The collected protein is treated as appropriate according to the intended use. The present enzyme thus obtained as a recombinant protein may be subjected to various modifications. For example, the present enzyme composed of a recombinant protein linked to any peptide or protein can be obtained by producing a recombinant protein using a vector into which a DNA encoding the present enzyme has been inserted together with other appropriate DNA. In addition, modification for causing addition of a sugar chain and/or a lipid, or N- or C-terminal processing may be carried out. These modifications allow, for example, extraction of a recombinant protein, simplification of purification, or addition of biological functions.

The present inventors have revealed the enzymological properties of the novel nucleosidases PN1 and PN2 which were successfully acquired. Therefore, the present enzymes PN1 and PN2 can also be characterized by the following enzymological properties.

<Enzymological Properties of PN1>
(1) Action
PN1 is a nucleosidase and catalyzes a reaction of hydrolyzing purine nucleosides into D-ribose and purine bases. The purine nucleoside is a glycoside in which a purine base and a reducing group of sugar are bound by an N-glycoside bond. Examples of the purine nucleoside include adenosine, guanosine, and inosine. In addition, the purine base is a generic term for bases having a purine skeleton, and specific examples thereof include adenine, guanine, hypoxanthine, and xanthine. In addition to purine nucleosides and purine bases, compounds having a purine skeleton including purine nucleotides and the like are collectively referred to as purine bodies.

PN1 shows activity even in the presence of adenosine, adenine, inosine, hypoxanthine, guanosine, guanine, and xanthine. In other words, PN1 is not subject to substantial inhibition by decomposition products. This characteristic feature is particularly important in applying the present enzymes to the production of foods and beverages. According to PN1 exhibiting this characteristic feature, it is possible to efficiently decompose the purine nucleosides derived from the raw materials in the production process of foods and beverages.

(2) Molecular Weight

PN1 contains a sugar chain (i.e., PN1 is a glycoprotein) in its natural form, and the molecular weight before removal of N-linked oligosaccharides was about 53 kDa (molecular weight measured by SDS-PAGE). The molecular weight is about 126 kDa when measured by gel filtration chromatography, and PN1 is presumed to form a dimer. On the other hand, the molecular weight, when measured by SDS-PAGE after removal of N-linked oligosaccharides, was about 49 kDa. Therefore, the molecular weight of the present enzyme when not containing N-linked oligosaccharides is about 49 kDa (molecular weight measured by SDS-PAGE).

(3) Optimum Temperature

The optimum temperature of PN1 is 55° C. to 60° C. This high optimum temperature as described above is advantageous in the application of PN1 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN1 maintains 80% or more activity under temperature conditions of 45° C. or lower. Therefore, for example, when the temperature during treatment is in the range of 5° C. to 45° C., the residual activity after the treatment becomes 80% or more.

On the other hand, when PN1 is treated in a phosphate buffer (pH 6.0) for 30 minutes, PN1 maintains 80% or more activity under the temperature conditions of 55° C. or lower. Therefore, for example, when the temperature during treatment is in the range of 5° C. to 55° C., the residual activity after the treatment becomes 80% or more.

PN1 which exhibits such excellent thermal stability can show high activity even under relatively high temperature conditions.

PN1 can be further characterized by the following enzymological properties (5) and (6).

(5) Optimum pH

The optimum pH of PN1 is 3.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN1 shows stable activity in a wide pH range. For example, if the pH of the enzyme solution to be treated is within the range of 3.5 to 7.5, PN1 shows 80% or more of the maximum activity after treatment at 30° C. for 30 minutes. Also, in the case of the treatment at 50° C. for 60 minutes, if the pH of the enzyme solution to be treated is within the range of 3.5 to 7.5, PN1 shows 80% or more of the maximum activity after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

<Enzymological Properties of PN2>

(1) Action

PN2 is a nucleosidase and catalyzes a reaction of hydrolyzing purine nucleosides into D-ribose and purine bases.

PN2 also shows activity in the presence of adenosine, adenine, inosine, hypoxanthine, guanosine, guanine, and xanthine. In other words, PN2 is not subject to substantial inhibition by decomposition products. This characteristic feature is particularly important in applying the present enzymes to the production of foods and beverages. According to PN2 exhibiting this characteristic feature, it is possible to efficiently decompose the purine nucleosides derived from the raw materials in the production process of foods and beverages.

(2) Molecular Weight

PN2 contains a sugar chain (i.e., PN2 is a glycoprotein) in its natural form, and the molecular weight before removal of N-linked oligosaccharides was about 51 kDa (molecular weight measured by SDS-PAGE). The molecular weight was about 230 kDa when measured by gel filtration chromatography. On the other hand, the molecular weight, when measured by SDS-PAGE after removal of N-linked oligosaccharides, was about 40 kDa. Therefore, the molecular weight of the present enzyme when not containing N-linked oligosaccharides is about 40 kDa (molecular weight measured by SDS-PAGE).

(3) Optimum Temperature

The optimum temperature of PN2 is 50° C. to 55° C. This high optimum temperature as described above is advantageous in the application of PN2 to the production of foods and beverages through a treatment process at a relatively high temperature. The optimum temperature can be evaluated by using an acetate buffer (pH 4.3) and also using guanosine as a substrate for quantitating the reaction product ribose.

(4) Thermal Stability

When treated in an acetate buffer (pH 4.5) for 60 minutes, PN2 maintains 80% or more activity under temperature conditions of 65° C. or lower. Therefore, for example, when the temperature during treatment is in the range of 5° C. to 65° C., the residual activity after the treatment becomes 80% or more.

On the other hand, when treated in a phosphate buffer (pH 6.0) for 30 minutes, PN2 maintains 80% or more activity under the temperature conditions of 55° C. or lower. Therefore, for example, when the temperature during treatment is in the range of 5° C. to 55° C., the residual activity after the treatment becomes 80% or more.

PN2 which exhibits such excellent thermal stability can show high activity even under relatively high temperature conditions.

PN2 can be further characterized by the following enzymological properties (5) and (6).

(5) Optimum pH

The optimum pH of PN2 is 4.5. The optimum pH is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

(6) pH Stability

PN2 shows stable activity in a wide pH range. For example, if the pH of the enzyme solution to be treated is within the range of 3.5 to 7.5, PN2 shows 80% or more of the maximum activity after treatment at 30° C. for 30 minutes. In addition, in the case of the treatment at 50° C. for 60 minutes, if the pH of the enzyme solution to be treated is within the range of 4.5 to 7.5, PN2 shows 80% or more of the maximum activity, after the treatment. The pH stability is determined based on the measurement results, for example, in a citrate buffer for the pH range of 2.5 to 3.5, in an acetate buffer for the pH range of 3.5 to 5.5, and in a potassium phosphate buffer for the pH range of 5.5 to 6.5.

The present enzyme preferably is nucleosidase derived from *Penicillium multicolor*. Here, by "nucleosidase derived from *Penicillium multicolor*" is meant a nucleosidase enzyme produced by a microorganism (of either a wild-type strain or a mutant strain) which is classified into *Penicillium multicolor*, or a nucleosidase enzyme obtained by genetic engineering procedures using the nucleosidase gene from a microorganism (of either a wild-type strain or a mutant strain) which is classified into *Penicillium multicolor*. Therefore, "nucleosidase derived from *Penicillium multicolor*" encompasses a recombinant enzyme that is produced by a host microorganism into which the nucleosidase gene (or a modified gene thereof) obtained from *Penicillium multicolor* has been introduced.

A strain of *Penicillium multicolor* is from which the present enzyme is derived is referred to as a producer strain for the inventive enzyme, for the purpose of description.

As shown in Examples described below, the present inventors have succeeded in isolating and purifying nucleosidases having the above properties from a *Penicillium multicolor* IFO 7569 strain. The *Penicillium multicolor* IFO 7569 strain is a bacterial strain (published as NBRC 7569 in the NBRC Culture catalog) stored in the National Institute of Technology and Evaluation (2-5-8 Kazusakamatari, Kisarazu, Chiba), and can be obtained through prescribed procedures.

3. Gene Encoding Nucleosidase, Recombinant DNA, and Transformant

The second aspect of the invention relates to a gene encoding the present enzyme. In one embodiment, the gene of the invention includes a DNA that encodes an amino acid sequence of SEQ ID NO: 1 or 2. Specific examples of the embodiment are the base sequence of SEQ ID NO: 3, which corresponds to the cDNA encoding the amino acid sequence of SEQ ID NO: 1, the base sequence of SEQ ID NO: 4, which corresponds to the genome DNA encoding the amino acid sequence of SEQ ID NO: 1, the base sequence of SEQ ID NO: 5, which corresponds to the cDNA encoding the amino acid sequence of SEQ ID NO: 2, and the base sequence of SEQ ID NO: 6, which corresponds to the genome DNA encoding the amino acid sequence of SEQ ID NO: 2.

The gene encoding the present enzyme is typically used in preparation of the present enzyme. According to a genetic engineering procedure using the gene encoding the present enzyme, the present enzyme in a more homogeneous state can be obtained. Further, the method can be a preferable method also in the case of preparing a large amount of the present enzyme. Note that uses of the gene encoding the present enzyme are not limited to preparation of the present enzyme. For example, the nucleic acid can also be used as a tool for an experiment intended for clarification of action mechanisms of the present enzyme or a tool for designing or preparing a mutant (modified form) of the present enzyme.

The "gene encoding the present enzyme" herein refers to a nucleic acid capable of obtaining the present enzyme when it is expressed, and includes, as a matter of course of a nucleic acid having a base sequence corresponding to the amino acid sequence of the present enzyme, also a nucleic acid obtained by adding a sequence that does not code for an amino acid sequence to such a nucleic acid. Degeneracy of a codon is also considered.

The gene of the present invention can be prepared in an isolated state by using a standard genetic engineering technique, a molecular biological technique, a biochemical technique, a chemical synthesis, a PCR method (e.g. an overlap extension PCR) or a combination thereof, with reference to sequence information disclosed in the present specification or attached sequence list.

In general, when a part of DNA encoding a certain protein is modified, a protein encoded by the modified DNA may sometimes have the equal function to that of a protein encoded by the DNA before modification. That is to say, the modification of the DNA sequence does not have a substantial effect on the function of the encoded protein, so that the function of the encoded protein may be maintained before and after the modification. Thus, as another embodiment, the present invention provides DNA encoding a protein having a base sequence equivalent to the reference base sequence (i.e., any one of SEQ ID NOs: 3 to 6) and having the nucleosidase activity (hereinafter, which is also referred to as "equivalent DNA"). The "equivalent base sequence" herein denotes a base sequence which is partly different from the reference base sequence but in which the function (herein, nucleosidase activity) of the protein encoded by the sequence is not substantially affected by the difference.

A specific example of the equivalent DNA includes DNA that hybridizes to the complementary base sequence of the reference base sequence under stringent conditions. Herein, the "stringent conditions" are referred to as conditions in which a so-called specific hybrid is formed but a nonspecific hybrid is not formed. Such stringent conditions are known to persons skilled in the art. Such stringent conditions can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15M NaCl, 15 mM sodium citrate, pH 7.0), 5×Denhardt solution, 1% SDS, 10% dextran sulfate, 10 µg/ml denatured salmon sperm DNA, and 50 mM phosphate buffer (pH 7.5)) is used and incubated at about 42° C. to about 50° C., thereafter, washed with 0.1×SSC and 0.1% SDS at about 65° C. to about 70° C. Further preferable stringent conditions can include, for example, a condition in which a hybridization solution 50% formamide, 5×SSC (0.15M NaCl, 15 mM sodium citrate, pH 7.0), 1×Denhardt solution, 1% SDS, 10% dextran sulfate, 10 µg/ml denatured salmon sperm DNA, and 50 mM phosphate buffer (pH 7.5)) is used.

Another specific example of the equivalent DNA can include DNA encoding a protein having a base sequence which includes substitution, deletion, insertion, addition or inversion in one or a plurality of bases (preferably one to several bases) in the reference base sequence, and which has a β-galactosidase activity. The substitution, deletion, or the like, of the base may occur in a plurality of sites. The "plurality" herein denotes, for example, 2 to 40 bases, preferably 2 to 20 bases, and more preferably 2 to 10 bases, although it depends upon the positions or types of the amino acid residue in the three-dimensional structure of the protein encoded by the DNA.

The equivalent DNA shows a 70% or more identity for example, preferably a 80% or more identity, more preferably a 90% or more identity, more and more preferably a 95% or more identity, and most preferably a 99% or more identity with the reference base sequence (i.e., any one of SEQ ID NOs: 3 to 6).

The above-mentioned equivalent DNA can be obtained by modifying the reference DNA so as to include substitution, deletion, insertion, addition and/or inversion of base by using treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York) and random mutagenesis (Molecular Cloning, Third Edition, Chapter 13, Cold Spring Harbor Laboratory Press, New York), and the like. Furthermore, the equivalent DNA can be also obtained by other methods such as irradiation with ultraviolet ray. A further example of the equivalent DNA can include DNA having difference in base as mentioned above due to polymorphism represented by SNP (single nucleotide polymorphism).

Another embodiment of the present invention relates to a nucleic acid having the complementary base sequence to the base sequence of the gene encoding the present enzyme. Another embodiment of the present invention provides a nucleic acid having a base sequence with an identity of at least about 60%, 70%, 80%, 90%, 95%, 99%, or 99.9% to the base sequence of the gene encoding the present enzyme or the complementary base sequence thereto.

Another aspect of the present invention relates to a recombinant DNA containing the gene of the present invention (the gene encoding the present enzyme). The recombinant DNA of the invention is provided in, for example, a form of a vector. The term "vector" in the present specification refers to a nucleic acid molecule that can transfer a nucleic acid inserted in the vector to a target such as a cell.

A suitable vector is selected according to its intended use (cloning, expression of a protein) and in consideration of a kind of host cell. Examples include a M13 phage or an altered form thereof, a λ, phage or an altered form thereof, and pBR322 or an altered form thereof (e.g., pB325, pAT153, pUC8), etc. as a vector having *Escherichia coli* as a host, pYepSec1, pMFa, and pYES2 as a vector having a yeast as a host, pAc, pVL, etc. as a vector having an insect cell as a host, and pCDM8, pMT2PC, etc. as a vector having a mammal cell as a host.

The vector of the present invention is preferably an expression vector. The "expression vector" refers to a vector capable of introducing a nucleic acid inserted in the expression vector into a target cell (host cell) and expressing it in the cell. The expression vector generally contains a promoter sequence necessary for expression of a nucleic acid inserted, an enhancer sequence for promoting expression, and the like. An expression vector containing a selective marker can also be used. When such an expression vector is used, presence or absence (and its degree) of introduction of the expression vector can be confirmed using a selective marker.

Insertion of DNA into the vector, insertion of a selective marker gene (if necessary), insertion of a promoter (if necessary), and the like can be performed by using a standard recombinant DNA technique (for example, a known method of using a restriction enzyme and a DNA ligase, which can be referred in Molecular Cloning, Third Edition, 1.84, Cold Spring Harbor Laboratory Press, New York).

The present invention further relates to a transformant into which the recombinant DNA, which contains the gene of the present invention, of the present invention is introduced. In the transformant of the preset invention, the gene of the present invention exists as an exogenous molecule. Preferably, the transformant of the present invention can be preferably prepared by transfection or transformation using the vector of the present invention mentioned above. The transfection and transformation can be carried out by, for example, a calcium phosphate coprecipitation method, electroporation (Potter, H. et al., Proc. Natl. Acad. Sci. U.S.A. 81, 7161-7165(1984)), lipofection (Feigner, P. L. et al., Proc. Natl. Acad. Sci. U.S.A. 84, 7413-7417 (1984)), microinjection (Graessmann, M. & Graessmann, A., Proc. Natl. Acad. Sci. U.S.A. 73, 366-370 (1976)), a method by Hanahan (Hanahan, D., J. Mol. Biol. 166, 557-580 (1983)), a lithium acetate method (Schiestl, R. H. et al., Curr. Genet. 16, 339-346 (1989)), protoplast-polyethylene glycol method (Yelton, M. M. et al., Proc. Natl. Acad. Sci. 81, 1470-1474 (1984)), and the like.

The host cell is not particularly limited as long as the present enzyme can be expressed, and it can be selected from, for example, *Bacillus* genus bacteria (e.g. *Bacillus subtilis, Bacillus licheniformis, Bacillus circulans*, etc.), lactic acid bacteria (e.g. *Lactococcus, Lactobacillus, Streptococcus, Leuconostoc, Bifidobacterium*, etc.), other bacteria (e.g. *Escherichia, Streptomyces*, etc.), yeast (e.g. *Saccharomyces, Kluyveromyces, Candida, Torula, Torulopsis*, etc.), and filamentous fungi (*Eumycetes*) (e.g. *Aspergillus* genus fungi such as *Aspergillus oryzae* and *Aspergillus niger, Penicillium* genus fungi, *Trichoderma* genus fungi, *Fusarium* genus fungi, etc.).

4. Method for Producing Nucleosidase

A fourth aspect of the present invention provides a method for producing a nucleosidase. One embodiment of the production method according to the present invention involves the step (step (1)) of culturing a producer microorganism for the present enzyme and the step (step (2)) of collecting the nucleosidase from the culture solution and/or the cell bodies after culture. The producer microorganism for the present enzyme is, for example, *Penicillium multicolor*, preferably a *Penicillium multicolor* IFO 7569 strain or a mutant strain thereof. The mutant strain can be obtained, for example, by irradiation with ultraviolet rays, X rays, γ rays, or the like and treatment with nitrous acid, hydroxylamine, N-methyl-N'-nitro-N-nitrosoguanidine, or the like. The mutant strain is not limited as long as it produces the present enzyme. Examples of the mutant strain include strains with improved productivity of the present enzyme, strains with reduced productivity of contaminants, strains which are easily cultured, and strains which are easily collected from a culture solution.

Conditions and methods for culturing cells of *Cryptococcus terrestris* are not particularly limited, as long as the inventive enzyme is produced. Thus, methods and culture conditions that are suitable for culturing a microorganism to be used can be set as appropriate, with the proviso that the inventive enzyme is produced. Although the culturing may be by either liquid culture or solid culture, liquid culture is preferably employed. Taking liquid culture as an example, culturing conditions therefor will be described below.

As the medium, any medium can be used as long as microorganisms to be used can grow. For example, a medium supplemented with a carbon source such as glucose, sucrose, gentiobiose, soluble starch, glycerin, dextrin, molasses, and organic acid; and further, a nitrogen source such as ammonium sulfate, ammonium carbonate, ammonium phosphate, ammonium acetate, or peptone, yeast extract, corn steep liquor, casein hydrolysate, bran, and meat extract; and furthermore, an inorganic salt such as potassium salt, magnesium salt, sodium salt, phosphate salt, manganese salt, iron salt, and zinc salt, and the like, can be used. In order to promote the growth of transformants to be used, vitamin, amino acid, and the like, may be added to the medium. The medium is cultured under the aerobic conditions such that the pH of the medium is adjusted to, for example, about 3 to 8 (preferably about 4 to 7), and the culture temperature is generally about 20° C. to 40° C. (preferably about 25° C. to 35° C.) for 1 to 20 days (preferably 3 to 10 days). An example of the culture method may include a shake culture method, and an aerobic submerged culture method by using a jar fermenter.

After culturing under the above conditions, the target protein is collected from the culture solution or the cell bodies (step (2)). When it is collected from the culture solution, the present enzyme can be obtained by separation and purification by removing insoluble matters by, for example, filtration of culture supernatant, centrifugation, and the like, followed by carrying out, for example, concentration by ultrafiltration membrane, salting out by ammonium sulfate precipitation, dialysis, various types of chromatography of an ion-exchange resin or an appropriate combination thereof. On the other hand, when it is collected from cell bodies, the target protein can be obtained by pulverizing the cell bodies by pressuring treatment, ultrasonic treatment, or the like, followed by separation and purification thereof similar to the above. After collection of the cell bodies from a culture solution by filtration, centrifugation, etc., a series of processes (pulverizing, separation, and purification of cell bodies) mentioned above may be carried out.

In another embodiment of the present invention, the nucleosidase is produced by using the above-mentioned transformant. In the production method in this embodiment, the transformant is cultured under the conditions such that a protein encoded by a gene introduced therein is produced (step (i)). The culture conditions of transformant are known as to various vector-host systems, and a person skilled in the art can easily set an appropriate culture condition. Following to the culturing step, the produced protein (nucleosidase) is collected (step (ii)). Collection and following purification can be conducted in the same manner as the above embodiment.

The purification degree of nucleosidase is not particularly limited. Furthermore, the final form of the β-galactosidase may be a liquid state or a solid state (including a powdery state).

The purified enzyme obtained as described above can be provided after being powdered, for example, by freeze dry, vacuum dry, or spray dry. In this time, the purified enzyme may be previously dissolved in a phosphoric acid buffer solution, a triethanol amine buffer solution, a tris-hydrochloric acid buffer solution, or a GOOD buffer solution. Preferably, a phosphoric acid buffer solution and a triethanol amine buffer solution can be used. Note that, for the GOOD buffer solution herein, PIPES, MES or MOPS is exemplified.

5. Enzyme Composition

The present enzyme is provided, for example, in the form of an enzyme composition. The enzyme composition contains the present enzyme as an active ingredient. The purification degree of the enzyme composition is not particularly limited. The enzyme composition may contain other ingredients as long as they do not have an influence on the effects of the present invention. Examples of the other ingredients include those derived from the medium and contaminating proteins. The form of the enzyme composition is not particularly limited. Examples of the form of the enzyme composition include liquid, powder and granule.

In one embodiment of the present enzyme composition, in order to obtain an enzyme composition through simple operations, an enzyme composition is produced by a production method including the following steps (I) and (II):

(I) culturing a producer microorganism for the present enzyme; and (II) removing the cell bodies after culture.

Since step (I) is similar to the above step (1) in the method for producing the present enzyme, the explanation thereof will be omitted. In step (II) following step (I), the cell bodies are removed by centrifugation, filtration, filter treatment, or the like. The thus-obtained culture solution containing no cell body is used as an enzyme composition as it is or after further treatment (i.e., the step (step (III)) of purifying the culture solution after removing the cell bodies). Examples of the further treatment referred to herein can include concentration with an ultrafiltration membrane. The liquid enzyme composition obtained in the above step (II) or step (III) may be subjected to a drying step (step (IV)) to prepare an enzyme composition in a powdery form, a granular form, or the like. Examples of the drying treatment here can include freeze drying, vacuum drying, spray drying, and the like.

6. Enzyme Preparation (Nucleosidase Preparation)

The present enzyme is provided, for example, in the form of an enzyme preparation (nucleosidase preparation). The enzyme preparation may contain an excipient, a buffer agent, a suspending agent, a stabilizer, a preservative, an antiseptic, saline, and the like besides the active ingredient (i.e. the present enzyme). The degree of purification of the present enzyme as the active ingredient is not particularly limited. Thus, the present enzyme may be a crude or purified enzyme. Examples of other enzymes include nucleosidases other than the present enzyme, amylases (α-amylase, β-amylase and glucoamylase), glucosidases (α-glucosidase and β-glucosidase), galactosidases (α-galactosidase and β-galactosidase), proteases (acidic protease, neutral protease and alkaline protease), peptidases (leucine peptidase and aminopeptidase), lipases, esterases, cellulases, nucleases, deaminases, oxidases, dehydrogenases, glutaminases, pectinases, catalases, dextranases, transglutaminases, protein deaminases, and pullulanases. As the excipient, lactose, sorbitol, D-mannitol, maltodextrin, white soft sugar, and the like can be used. As the buffer agent, phosphates, citrates, acetates, and the like can be used. As the stabilizer, propylene glycol, ascorbic acid, and the like can be used. As the preservative, phenol, benzalkonium chloride, benzyl alcohol, chlorobutanol, methylparaben, and the like can be used. As the antiseptic, benzalkonium chloride, paraoxybenzoic acid, chlorobutanol, and the like can be used.

In one embodiment of the present enzyme preparation, in order to obtain a liquid enzyme preparation through simple operations, an enzyme preparation is produced by a production method including the following steps (I) and (II):

(I) culturing a producer microorganism for the present enzyme; and (II) removing the cell bodies after culture.

Since step (I) is similar to the above step (1) in the method for producing the present enzyme, the explanation thereof will be omitted. In step (II) following step (I), the cell bodies are removed by centrifugation, filtration, filter treatment, or the like. The thus-obtained culture solution containing no cell body is used as an enzyme preparation as it is or after further treatment (i.e., the step (step (III)) of purifying the culture solution after removing the cell bodies). Examples of the further treatment referred to herein can include concentration with an ultrafiltration membrane. The liquid enzyme preparation obtained in the above step (II) or step (III) may be subjected to a drying step (step (IV)) to prepare an enzyme preparation in a powdery form, a granular form, or the like. Examples of the drying treatment here can include freeze drying, vacuum drying, spray drying, and the like.

EXAMPLES

1. Acquisition of New Nucleosidase

More than 10,000 kinds of microorganisms were screened in order to find a novel nucleosidase. As a result, four strains of microorganisms, i.e., a *Penicillium multicolor* IFO 7569 strain, a *Bacillus brevis* IFO 15304 strain, a *Brevibacillus linens* IFO 12141 strain, and a *Mucor javanicus* 4068 strain were identified as promising candidates. The nucleosidases produced by these microorganisms were evaluated in terms of the action and effect.

(1) Method for Culturing *Penicillium multicolor* IFO 7569 Strain

A *Penicillium multicolor* IFO 7569 strain was inoculated into 100 mL of the following culture medium B and cultured with shaking in a Sakaguchi flask with a volume of 500 mL at 27° C. for 48 to 72 hours. This preculture solution was transferred to 2 L of the following culture medium B and cultured with aeration and agitation at 27° C. for 120 to 188 hours. This culture solution was filtered through diatomaceous earth to remove cell bodies. The culture supernatant obtained after removal of the cell bodies was concentrated with an ultrafiltration membrane to obtain a lyophilized powder.

<Culture Medium A>
1% Lustergen FK (Nippon Starch Chemical Co., Ltd.)
1% Yeast extract (Difco)
0.5% NaCl
pH7.0
<Culture Medium B>
1% Lustergen FK (Nippon Starch Chemical Co., Ltd.)
1% Yeast extract (Difco)
2% Cornmeal (Matsumoto Nosan K.K.)
0.5% NaCl
pH6.5

(2) Method for Culturing *Bacillus brevis* IFO 15304 Strain, *Brevibacillus* Linens IFO 12141 Strain, and *Mucor javanicus* 4068 Strain A *Bacillus brevis* IFO 15304 strain and a *Brevibacillus linens* IFO 12141 strain were each inoculated into 10 mL of the above culture medium A and cultured with shaking at 30° C. for 48 hours in a test tube. On the other hand, a *Mucor javanicus* IFO 4068 strain was inoculated into 10 mL of the above culture medium B and cultured under the same conditions. The culture solutions were each transferred to 50 mL of the main culture medium having the same composition and cultured with shaking at 30° C. for 120 hours. The culture solutions were centrifuged to remove cell bodies, and freeze-dried powders were obtained from the supernatants after removal of the cell bodies.

(3) Measurement of Nucleosidase Activity

The nucleosidase activity was defined by quantitating ribose produced by a reaction using guanosine as a substrate. In 1 mL of a reaction solution, a 0.1M acetate buffer (pH 4.3), 8 mM of guanosine, and an appropriate amount of an enzyme are contained. The reaction started with addition of guanosine, and carried out at 55° C. for 30 minutes. The reaction was stopped by adding 1.5 mL of a 0.5% dinitro salicylic acid solution, and then the solution was boiled for 10 minutes. The absorbance at 540 nm of the reaction solution after cooling was measured, and the activity value was calculated from the value obtained by subtracting the absorbance of an enzyme-free reaction solution. The amount of the enzyme producing 1 μmol of ribose in 30 minutes was defined as 1 U of enzyme activity.

(4) Study on Properties of Nucleosidase Derived from *Penicillium multicolor* IFO 7569 Strain (*P. multicolor* Nucleosidase)

In order to investigate the properties of the *P. multicolor* nucleosidase, a purine body solution having the following composition was used to study the operative temperature range and the operative pH range.

Adenosine 0.08 mmol/L
Adenine 0.43 mmol/L
Inosine 0.49 mmol/L
Hypoxanthine 0.08 mmol/L
Guanosine 0.67 mmol/L
Guanine 1.45 mmol/L
Xanthosine 0.00 mmol/L
Xanthine 0.08 mmol/L (4-1) Operative Temperature Range To 2 mL of the purine body solution, 9 U of the *P. multicolor* nucleosidase was added to cause a reaction at pH 5.5 for 1 hour at each temperature, then diluted 10 times with a 150 mM sodium phosphate buffer (pH 2.5) as the mobile phase of HPLC, and quantitatively analyzed by high performance liquid chromatography. The free purine base ratio was calculated based on the following calculation formula. At the reaction temperature of 50° C. to 60° C., the free purine base ratio became 90% or more (FIG. 1).

Free purine base ratio (%)={purine base/(purine nucleoside+purine base)}×100.

(4-2) Operative pH Range

Figure 2:
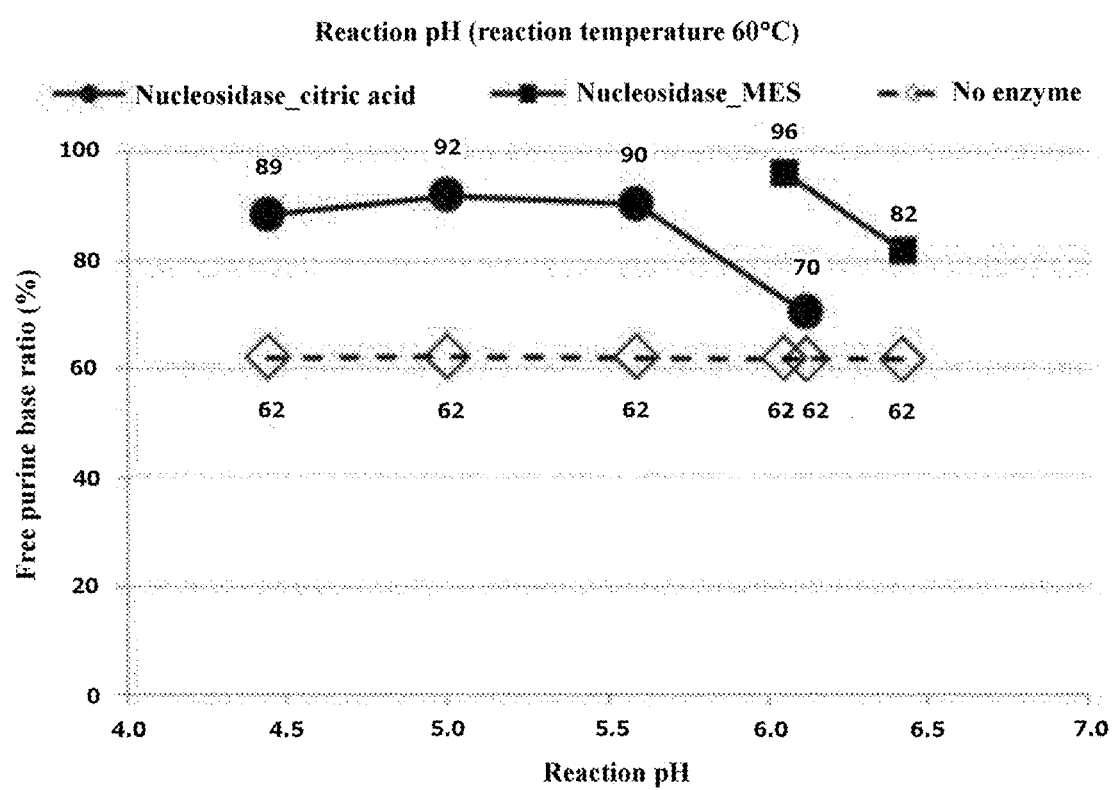
FIG. 2 Operative pH range of the nucleosidase derived from the *Penicillium multicolor* IFO 7569 strain. An enzymatic reaction was carried out under each pH condition in the presence of seven kinds of purine bodies, and the free purine base ratio was determined.

To 2 mL of the purine body solution, 9 U of the *P. multicolor* nucleosidase was added to cause a reaction at 55° C. for 1 hour at each pH, then diluted 10 times with a 150 mM sodium phosphate buffer (pH 2.5) as the mobile phase of HPLC, and quantitatively analyzed by high performance liquid chromatography. A citrate buffer was used when the pH was 4.5 to 6.0, and an MES buffer was used when the pH was 6.0 to 6.5. As in the case of the study on the operative temperature range, the free purine base ratio was calculated. In the citrate buffer, the free purine body ratio was 80% or more when the pH was 4.5 to 5.5. In the MES buffer, the free purine body ratio was 80% or more when the pH was 6.0 to 6.5 (FIG. 2).

Figure 3:
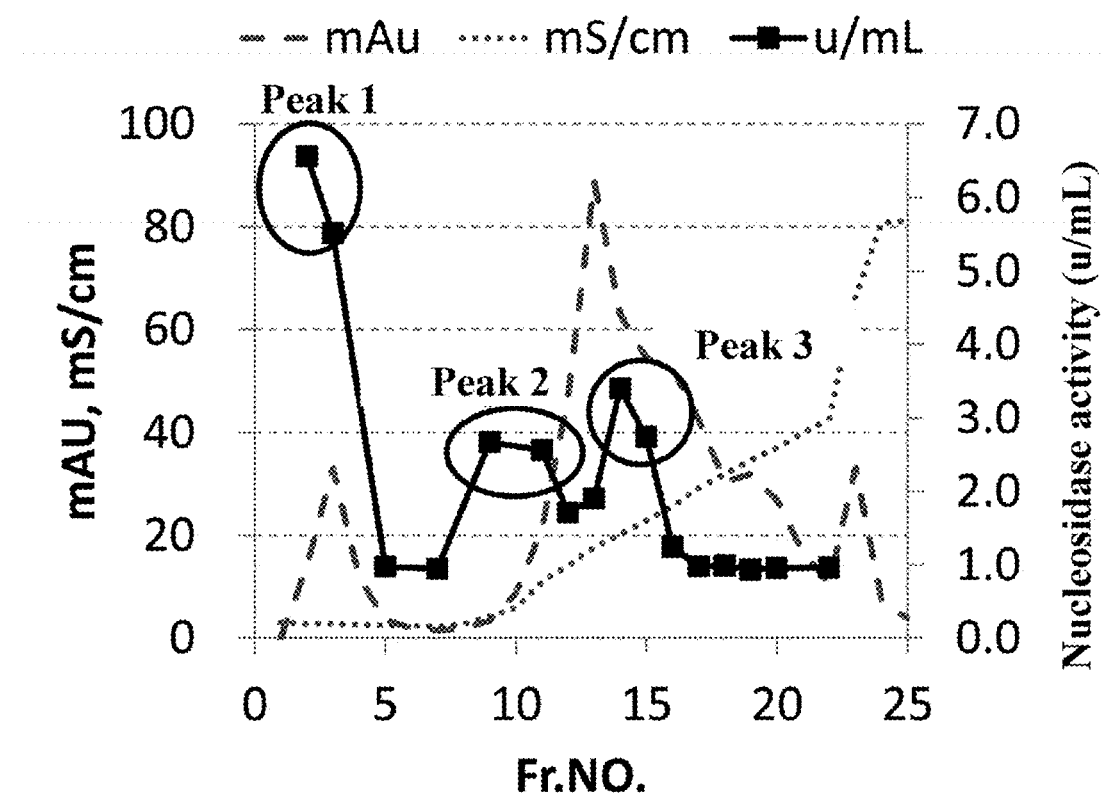
FIG. 3 Purification of the nucleosidase from the *Penicillium multicolor* IFO 7569 strain. This figure shows the results of DEAE HP column chromatography.

(5) Purification of Nucleosidase Derived from *Penicillium multicolor* IFO 7569 Strain The nucleosidase was purified by hydroxyapatite column, anion exchange column, hydrophobic column, and gel filtration column chromatographies. A series of purification processes will be shown below. First, 0.1 g of the lyophilized powder prepared from the culture solution of the *Penicillium multicolor* IFO 7569 strain was dissolved in 5 mL of a buffer (5 mM potassium phosphate buffer (pH 6)+0.3M NaCl), and the solution was applied to a hydroxyapatite column (Bio-Rad) equilibrated with the same buffer. The adsorbed protein was eluted with a phosphoric acid gradient of 5 mM to 300 mM, and an active fraction was collected. The obtained active fraction was dialyzed against a buffer (20 mM potassium phosphate buffer (pH 5.5)) and applied to a DEAE HP column (GE Healthcare) equilibrated with the same buffer. When the adsorbed protein was eluted with an NaCl gradient of 0 mM to 500 mM, three peaks were observed (FIG. 3). Fr. 2 was defined as peak 1, Fr. 8 and Fr. 9 as peak 2, and Fr. 14 and Fr. 15 as peak 3.

Figure 4:
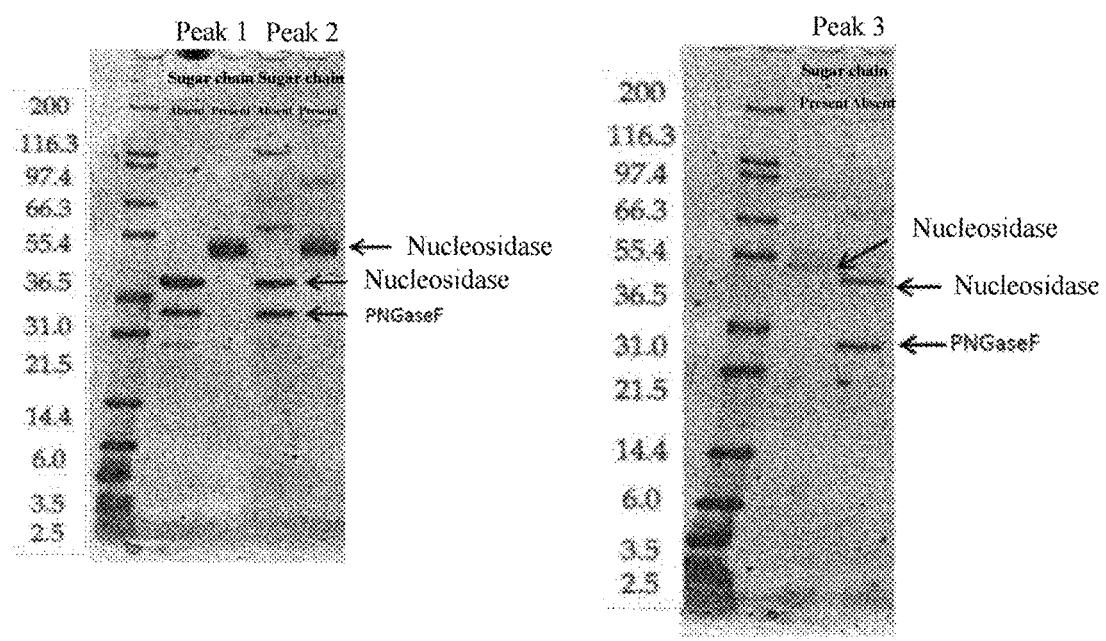
FIG. 4 Measurement results of the molecular weight of each purified enzyme (peaks 1 to 3) (SDS-PAGE). The left shows the results of peaks 1 and 2. The right shows the results of peak 3. A sample after PNGase F treatment ("sugar chain absent" lane) and an untreated sample ("sugar chain present" lane) were electrophoresed and stained with CBB. The leftmost lane shows molecular weight markers (myosin (200 kDa), β-galactosidase (116.3 kDa), phosphorylase B (97.4 kDa), BSA (66.3 kDa), glutamate dehydrogenase (55.4 kDa), lactic acid dehydrogenase (36.5 kDa), carbonate anhydrase (31.0 kDa), trypsin inhibitor (21.5 kDa), lysozyme (14.4 kDa), aprotinin (6.0 kDa), insulin B chain (3.5 kDa), and insulin A chain (2.5 kDa)).

The collected peak 3 was dialyzed against a buffer (20 mM acetate buffer (pH 4.5)+30% saturated ammonium sulfate), and applied to a Phenyl HP column (GE Healthcare)

equilibrated with the same buffer. The adsorbed protein was eluted with an ammonium sulfate gradient of 30% saturation to 0%, and the active fraction was collected. The obtained active fraction was dialyzed with a buffer (20 mM sodium phosphate buffer (pH 6)) and then concentrated to 0.5 mL using an ultrafiltration membrane. The concentrated active fraction was applied to HiLoad 16/60 Superdex 200 (GE Healthcare) equilibrated with the same buffer, and an active fraction was collected. The obtained purified enzyme was confirmed to show a single band by SDS-PAGE (FIG. 4). The molecular weight was estimated to be about 53 kDa by SDS-PAGE and about 126 kDa by gel filtration chromatography (FIG. 5). The sugar chains of the resultant purified enzyme were removed with PNGase F (New England Bio-Labs). The treatment method was in accordance with the attached protocol. By SDS-PAGE after the treatment, it was shown that the molecular weight decreased from about 53 kDa to about 49 kDa by removal of the N-linked oligosaccharides (FIGS. 4 and 5). The collected peaks 1 and 2 were similarly purified, and their molecular weight was determined by SDS-PAGE and gel filtration chromatography. The molecular weight was estimated to be about 51 kDa by SDS-PAGE and about 230 kDa by gel filtration chromatography (FIG. 5). The sugar chains of the resultant purified enzyme were removed with PNGase F (New England Bio-Labs). By SDS-PAGE after the treatment, it was shown that the molecular weight was reduced from about 51 kDa to about 40 kDa by removal of the N-linked oligosaccharides (FIGS. 4 and 5).

When the N-terminal amino acid sequence of the respective purified enzymes (peaks 1 to 3) were analyzed with a protein sequencer (Shimadzu Corporation), the following sequences were estimated.

```
N-terminal amino acid sequence of peak 1:
                                     (SEQ ID NO: 7)
ADKHYAIMDNDWYTA N-terminal amino acid sequence of peak 2:
                                     (SEQ ID NO: 8)
ADKHYAIMDNDWYTA N-terminal amino acid sequence of peak 3:
                                     (SEQ ID NO: 9)
VETKLIFLT
```

Peak 1 and peak 2 had the same molecular weight and N-terminal amino acid sequence, and thus were estimated to be the same enzymes (FIG. 5). In the subsequent study, the enzymes were called PN2, and the enzyme of peak 3 was called PN1.

2. Gene Cloning

The following degenerate primers were designed from the determined N-terminal amino acid sequences and nucleosidase conserved sequences, and PCR was carried out using the *P. multicolor* genomic DNA as a template.

```
<Degenerate primer for PN1>
FW:
                                    (SEQ ID NO: 10)
ACIAARTAYMGNTTYYTIAC RV:
                                    (SEQ ID NO: 11)
CATNCCNCKNGTCCAYTGNCC
```

```
<Degenerate primer for PN2>
FW:
                                    (SEQ ID NO: 12)
GCNATHATGGAYAAYGAYTGGTAYAC RV:
                                    (SEQ ID NO: 13)
GCNGCNGTYTCRTCCCARAANGG
```

The obtained amplified fragments were subcloned into pMD20-T (TaKaRa) and sequenced. Southern blotting and colony hybridization were carried out using the probes shown in FIG. 6. The obtained fragments were sequenced to identify the base sequences (FIG. 7) in the genomes of PN1 and PN2.

Next, cDNA was prepared from mRNA prepared from the *P. multicolor* genomic DNA using SMARTER RACE 5'/3' (TaKaRa). Then, PCR was carried out using the following primers, and the amplified fragments were sequenced to determine the base sequences of PN1 and PN2 in the cDNA (FIG. 8). From the determined base sequences, amino acid sequences of PN1 and PN2 were identified (FIG. 9). In FIG. 10, PN1 and PN2 were compared.

```
<PCR primer for PN1>
FW:
                                    (SEQ ID NO: 14)
ATGGCACCTAAGAAAATCATCATTG RV:
                                    (SEQ ID NO: 15)
TTAGTGGAAGATTCTATCGATGAGG <PCR primer for PN2>
FW:
                                    (SEQ ID NO: 16)
ATGCATTTCCCTGTTTCATTGCCGC RV:
                                    (SEQ ID NO: 17)
TCAACGCTCATTTCTCAGGTCGG
```

3. Study on Various Properties of Enzyme PN1

(1) Optimum Temperature

Figure 11:
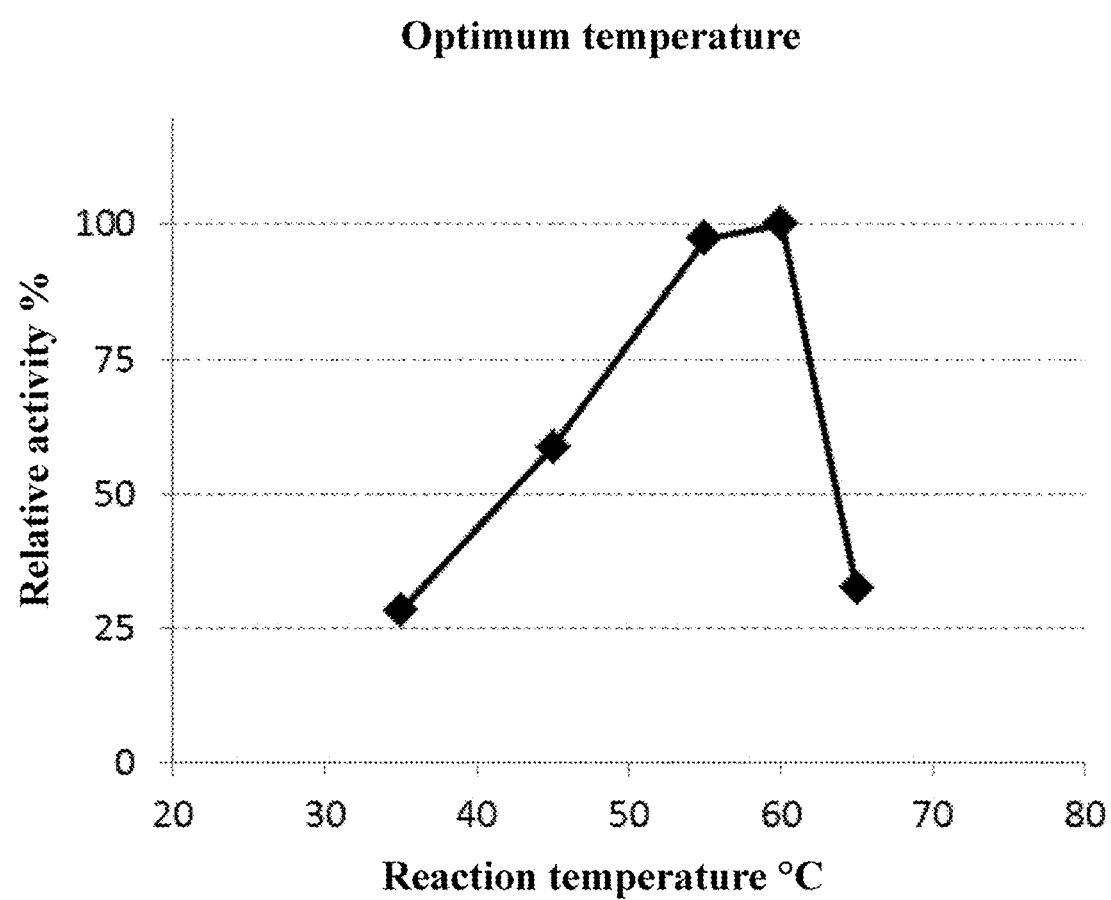
FIG. 11 Optimum temperature of the purified enzyme (PN1).

The optimum temperature of the nucleosidase (PN1) of peak 3 collected from the DEAE HP column was analyzed. The results at the respective temperatures are shown in FIG. 11. The optimum temperature under the conditions was 55° C. to 60° C.

(2) Thermal Stability

Figure 12:
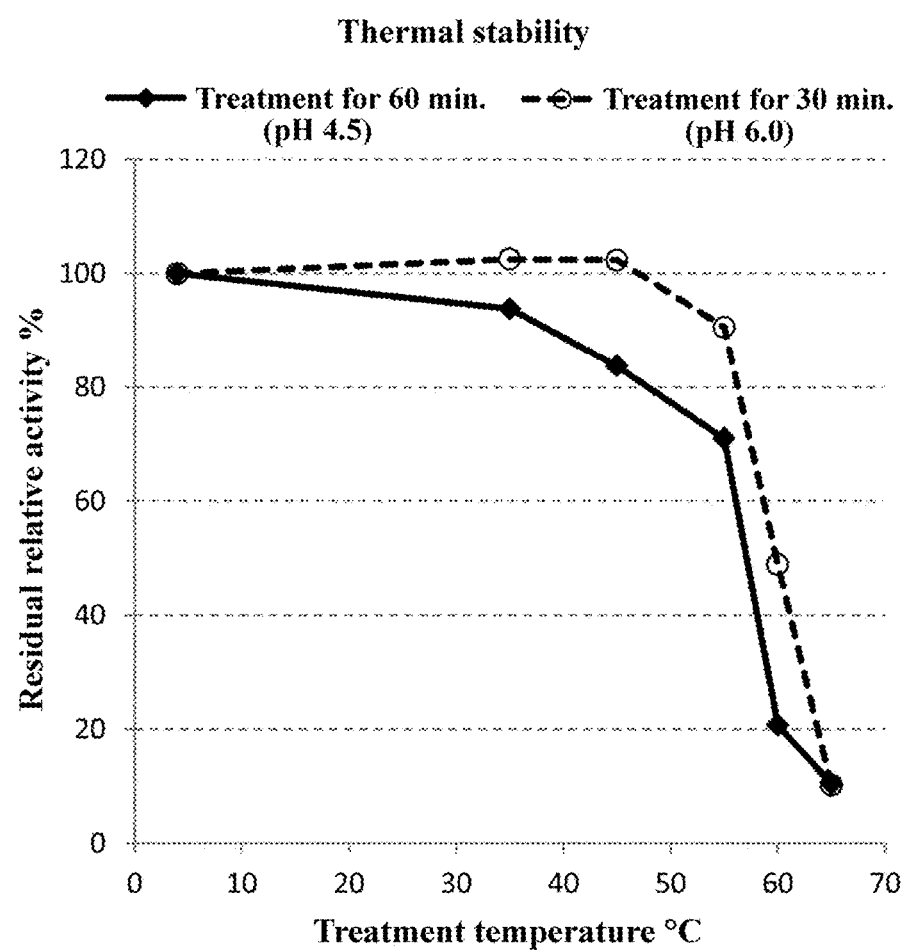
FIG. 12 Thermal stability of the purified enzyme (PN1).

The thermal stability of the nucleosidase of peak 3 collected from the DEAE HP column was analyzed. PN1 showed residual activity of 80% at up to 45° C. when treated at pH 4.5 for 60 minutes and at up to 55° C. when treated at pH 6.0 for 30 minutes (FIG. 12).

(3) Optimum pH

Figure 13:
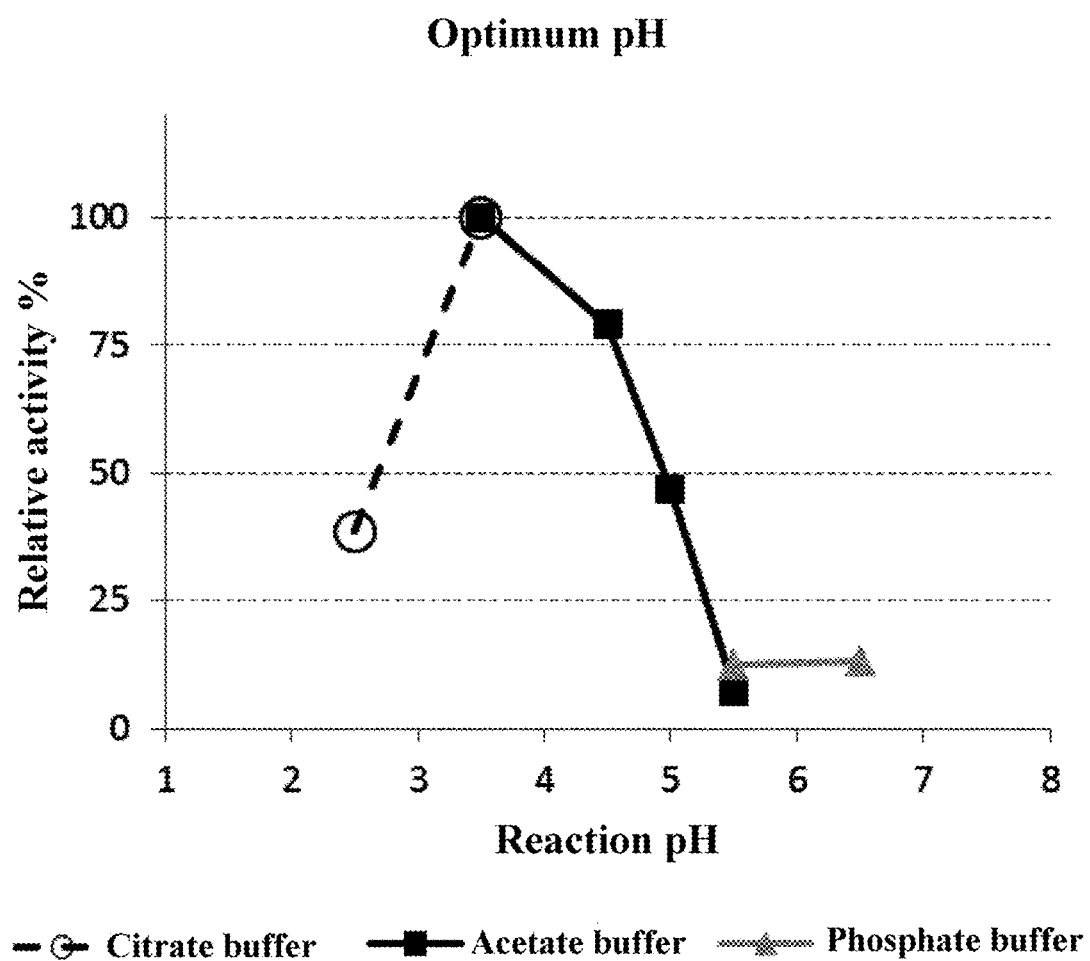
FIG. 13 Optimum pH of the purified enzyme (PN1).

The optimum pH of the nucleosidase of peak 3 collected from the DEAE HP column was analyzed. A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was 3.5 (FIG. 13).

(4) pH Stability

Figure 14:
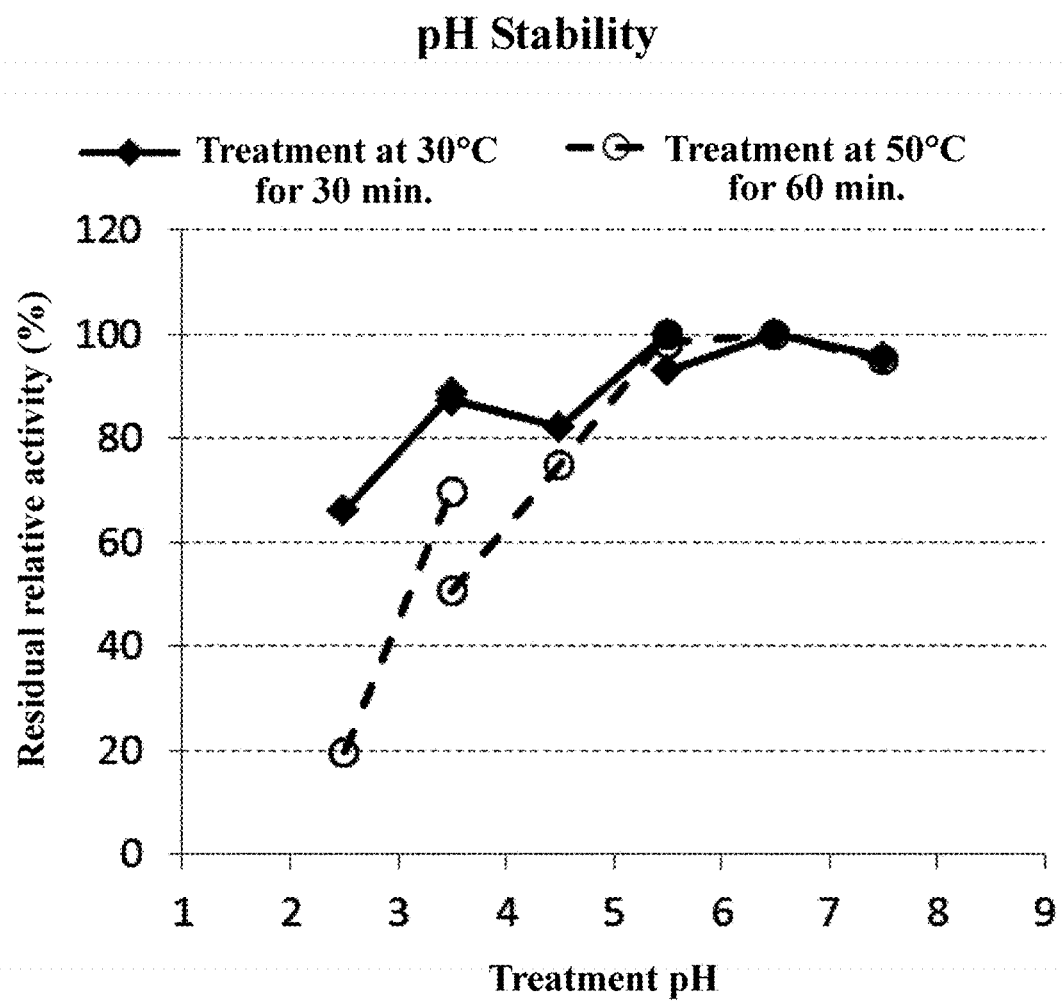
FIG. 14 pH Stability of the purified enzyme (PN1).

The pH stability of the nucleosidase of peak 3 collected from the DEAE HP column was analyzed when treatment was carried out at 30° C. for 30 minutes and at 50° C. for 60 minutes, respectively, at each pH. The same buffers were used as those used for the study on the optimum pH, and a potassium phosphate buffer was used for pH 7.5. PN1 showed residual activity of 80% or more at a pH of 3.5 to 7.5 when treated at 30° C. for 30 minutes and a pH of 3.5 to 7.5 when treated at 50° C. for 60 minutes (FIG. 14).

4. Recombinant Production of Enzyme PN2

Figure 15:
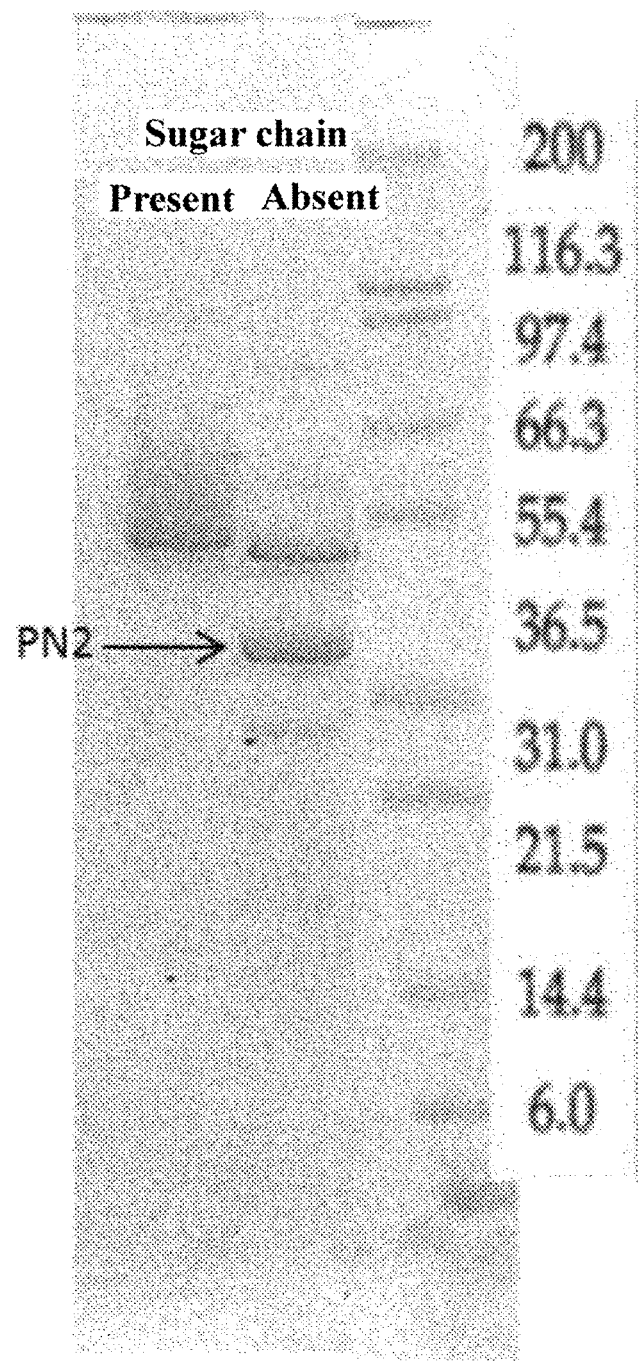
FIG. 15 Results of electrophoresis of the recombinantly produced enzyme (PN2).

The cDNA fragment of PN2 was inserted into the cloning site of an expression vector to construct a PN2 expression vector. The expression vector was used to transform *Aspergillus oryzae* (*A. oryzae* (pyrG−)). The obtained transformant was cultured in liquid for 4 days (30° C., 300 rpm). The culture supernatant was collected to measure the nucleosidase activity. As a result, it was revealed that a transformant showing activity was obtained. In addition, when the culture supernatant was subjected to sugar chain removal treatment and electrophoresis, a band having a size consistent with the estimated molecular weight was confirmed (FIG. 15).

5. Study on Various Properties of Enzyme PN2

Recombinantly produced PN2 was used to study various properties. Experiment method, conditions, etc. were the same as in the case of the study on PN1.

(1) Optimum Temperature

Figure 16:
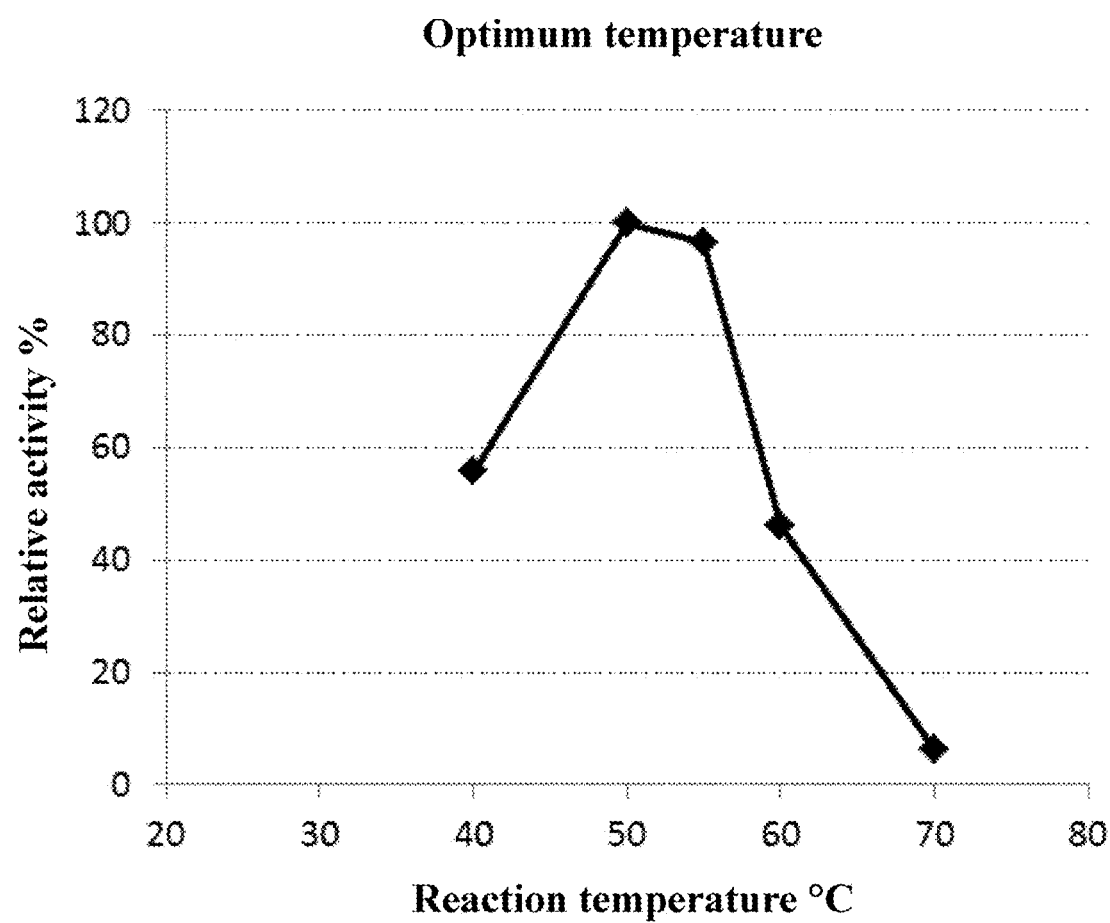
FIG. 16 Optimum temperature of the purified enzyme (PN2).

The optimum temperature was 50° C. to 55° C. (FIG. 16).

(2) Thermal Stability

Figure 17:
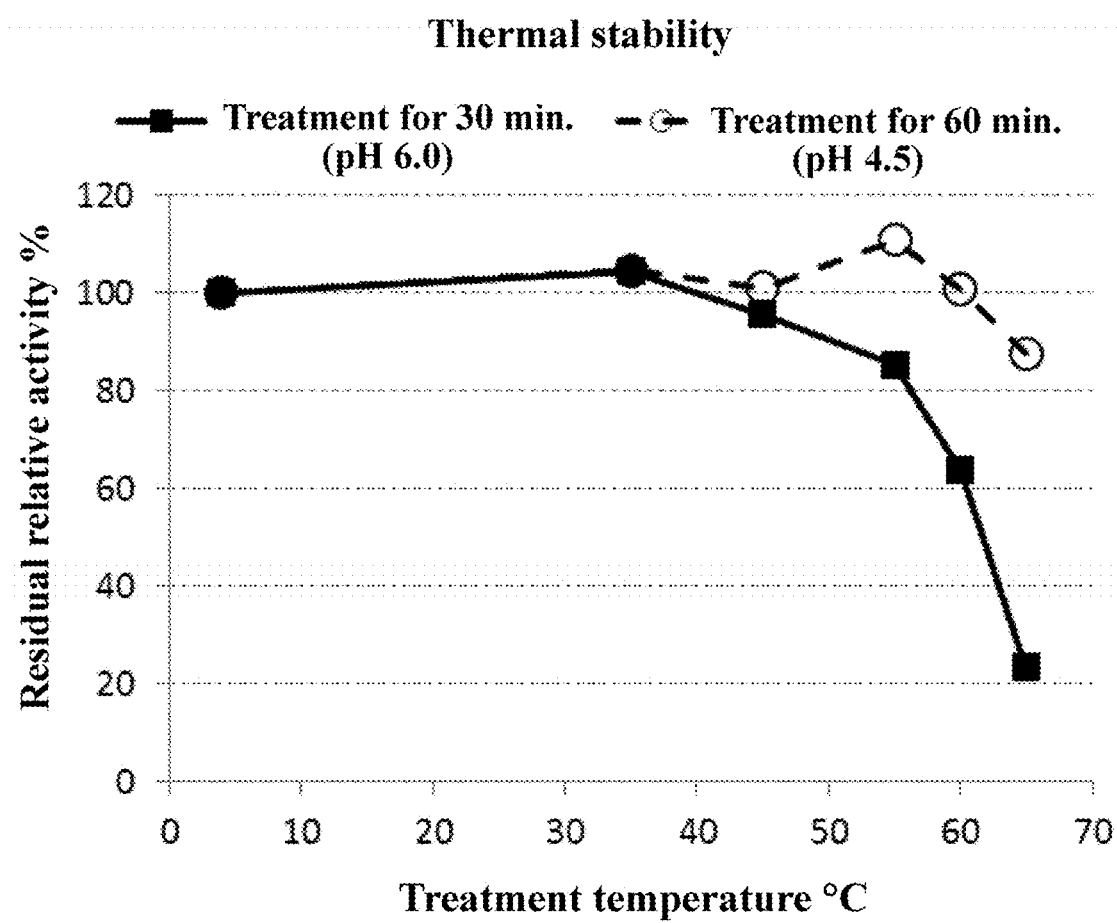
FIG. 17 Thermal stability of the purified enzyme (PN2).

PN2 showed residual activity of 80% at up to 65° C. when treated at pH 4.5 for 60 minutes and at up to 55° C. when treated at pH 6.0 for 30 minutes (FIG. 17).

(3) Optimum pH

Figure 18:
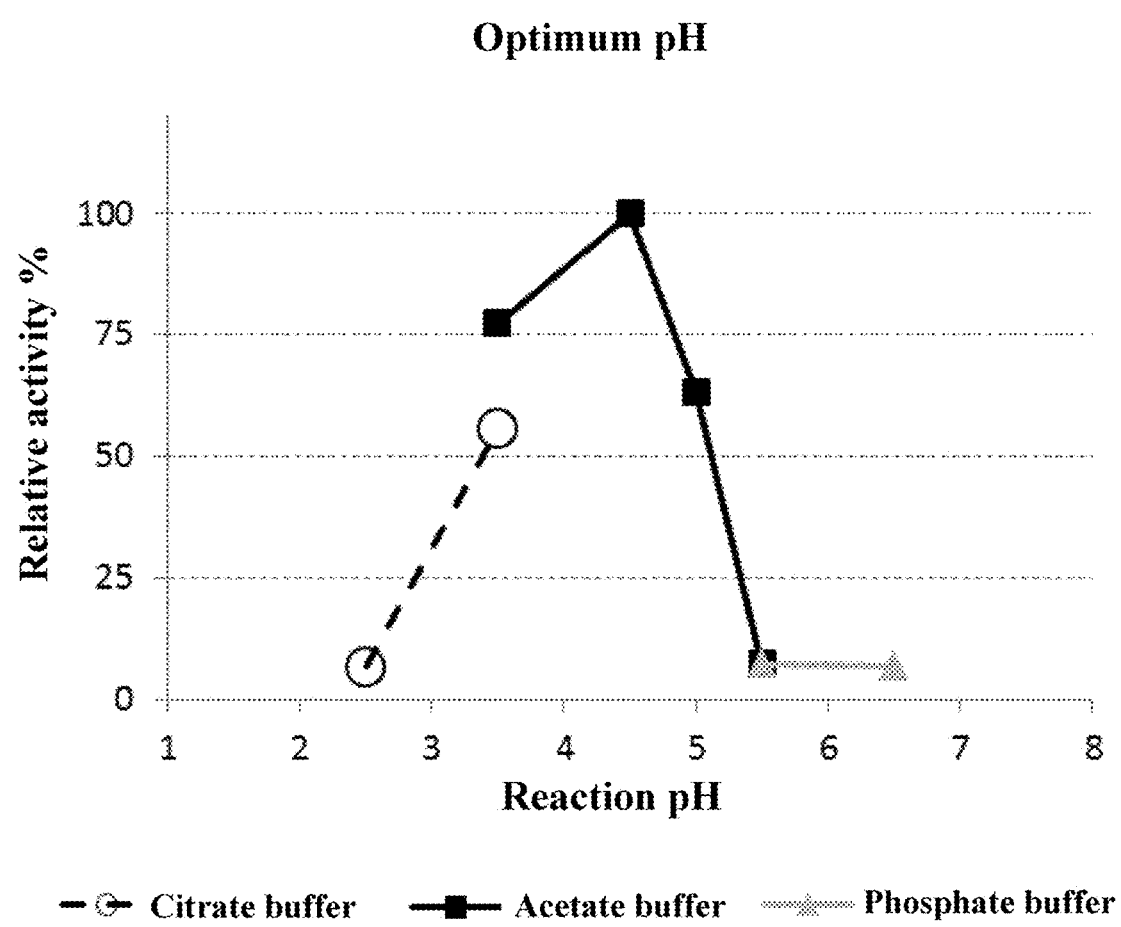
FIG. 18 Optimum pH of the purified enzyme (PN2).

A citrate buffer was used for pH 2.5 and pH 3.5, an acetate buffer was used for pH 3.5, pH 4.5, and pH 5.5, and a potassium phosphate buffer was used for pH 5.5 and pH 6.5. The optimum pH was 4.5 (FIG. 18).

(4) pH Stability

Figure 19:
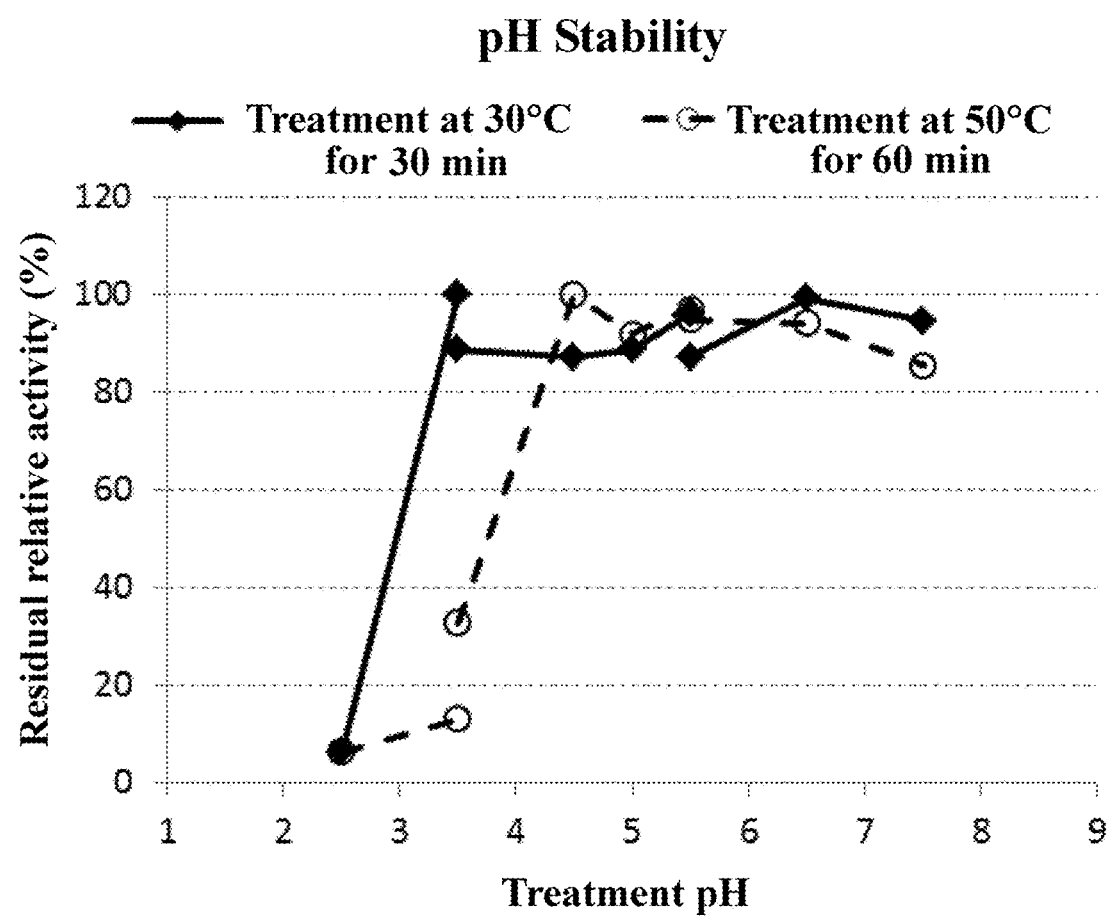
FIG. 19 pH Stability of the purified enzyme (PN2).

The pH stability was analyzed when treatment was carried out at 30° C. for 30 minutes and at 50° C. for 60 minutes, respectively, at each pH. The same buffers were used as those used for the study on the optimum pH. PN2 showed residual activity of 80% or more at a pH of 3.5 to 7.5 when treated at 30° C. for 30 minutes and a pH of 4.5 to 7.5 when treated at 50° C. for 60 minutes (FIG. 19).

6. Change in Taste by Nucleosidase

It was studied whether a nucleosidase could be used to increase the taste of a yeast extract and to impart a new taste.

(1) Method

A 1.5% ribonucleic acid (Wako Pure Chemical Industries) solution (pH 5.5) was prepared, and nuclease "Amano" G (Amano Enzyme Inc.) was added thereto in a proportion of 2% relative to the weight of the ribonucleic acid to carry out a reaction at 70° C. for 3 hours. Subsequently, the reaction solution was adjusted to have a pH of 6.0, and Deamizyme G (Amano Enzyme Inc.) was added thereto in a proportion of 0.4% relative to the weight of the ribonucleic acid to carry out a reaction at 50° C. for 3 hours. Thereafter, boiling treatment was carried out for 20 minutes to deactivate the enzyme. To the reaction solution was added the above-described nucleosidase (mixture of PN1 and PN2) (4,000 U/g) in a proportion of 0.4% relative to the amount of the reaction solution to carry out a reaction at 50° C. for 1 hour. For deactivation of the nucleosidase, the reaction solution was boiled for 10 minutes. The reaction solution to which a heat-deactivated nucleosidase was added was used as a control. The taste of the sample prepared by the above method was evaluated. The amount of the enzyme producing 1 μmol of ribose in 30 minutes using guanosine as a substrate is defined as 1 U of nucleosidase activity.

(2) Result

When sensory evaluation was carried out by 8 panelists, the result that the nucleosidase-added group was stronger in taste than the control group was obtained (FIG. 20).

In addition, as a result of HPLC analysis, it could be confirmed that purine nucleotides (GMP, AMP, and IMP) were decomposed into purine bases (adenine, guanine, and hypoxanthine) by the nucleosidase treatment. This result also supports that the nucleosidase used catalyzes the reaction of hydrolyzing purine nucleotides into purine bases and D-ribose-5-phosphate.

From the above results, it was suggested that a yeast extract improved in taste or enhanced in umami could be obtained by adding nucleosidase treatment to the yeast extract production process.

INDUSTRIAL APPLICABILITY

According to the production method of the present invention, a nucleic acid-based seasoning having a characteristic taste can be obtained. The nucleic acid-based seasoning obtained by the production method of the present invention can be used for enhancement and adjustment of the taste of various foods and beverages.

The present invention is not limited to the description of the embodiments and example of the present invention at all. Various modifications that can be easily achieved by those skilled in the art without departing from the claims also fall within the scope of the invention. The contents of the articles, patent laid-open publications, patent publications, and the like specified herein shall be cited by incorporation in their entity.

The invention claimed is:

1. A method for producing a nucleic acid-based seasoning, comprising a step of increasing the content of purine bases in a final product of the nucleic acid-based seasoning produced by the method, which contribute to the overall taste in the nucleic acid-based seasoning, by treating a ribonucleotide-containing material with nucleosidase.

2. The production method according to claim 1, wherein the ribonucleotide-containing material is a ribonuclease-treated ribonucleic acid-containing material.

3. The production method according to claim 2, comprising the following steps (1) and (2):
(1) providing a ribonucleotide-containing material obtained by treating a ribonucleic acid-containing material with a ribonuclease; and (2) treating the ribonucleotide-containing material with an AMP-deaminase and a nucleosidase separately or simultaneously.

4. The production method according to claim 3, wherein step (2) comprises the following steps (2-1) and (2-2):
(2-1) treating the ribonucleotide-containing material with an AMP-deaminase, and (2-2) treating the treated product after step (2-1) with a nucleosidase.

5. The production method according to claim 1, wherein the ribonucleotide-containing material is a ribonucleic acid-containing material treated with a ribonuclease and an AMP-deaminase.

6. The production method according to claim 1, wherein the ribonucleotide-containing material comprises purine nucleotides.

7. The production method according to claim 1, wherein the ribonucleic acid-containing material is a yeast lysate.

8. The production method according to claim 1, wherein the nucleosidase is a protein that comprises the amino acid sequence of SEQ ID NO: 1 or an equivalent amino acid sequence having 90% or more identity with the amino acid sequence, or the amino acid sequence of SEQ ID NO: 2 or an equivalent amino acid sequence having 90% or more identity with the amino acid sequence.

9. The production method according to claim 8, wherein the amino acid sequence of the protein is an equivalent amino acid sequence having 95% or more identity with the amino acid sequence of SEQ ID NO: 1 or the amino acid sequence of SEQ ID NO: 2.

10. The production method according to claim 1, wherein the nucleosidase has the following enzymological properties:
(1) action: catalyzing a reaction of hydrolyzing purine nucleosides into D-ribose and purine bases;
(2) molecular weight: about 49 kDa (by SDS-PAGE) when the nucleosidase does not contain N-linked oligosaccharides;
(3) optimum temperature: 55° C. to 60° C.; and
(4) thermal stability: stable at 55° C. or lower (pH 6.0, for 30 minutes).

11. The production method according to claim 10, wherein the nucleosidase further has the following enzymological properties:
(5) optimum pH: 3.5; and
(6) pH stability: stable in the range of pH 3.5 to 7.5 (30° C., for 30 minutes).

12. The production method according to claim 1, wherein the nucleosidase has the following enzymologic al properties:
(1) action: catalyzing a reaction of hydrolyzing purine nucleosides into D-ribose and purine bases;
(2) molecular weight: about 40 kDa (by SDS-PAGE) when the nucleosidase does not contain N-linked oligosaccharides;
(3) optimum temperature: 50° C. to 55° C.; and
(4) thermal stability: stable at 65° C. or lower (pH 4.5, for 60 minutes).

13. The production method according to claim 12, wherein the nucleosidase further has the following enzymological properties:
(5) optimum pH: 4.5; and
(6) pH stability: stable in the range of pH 3.5 to 7.5 (30° C., for 30 minutes).

14. The production method according to claim 1, wherein the nucleosidase is derived from *Penicillium* multicolor.

15. The production method according to claim 14, wherein the *Penicillium* multicolor is an IFO 7569 strain.

16. A nucleic acid-based seasoning obtained by the production method according to claim 1.

17. A method for producing a nucleic acid-based seasoning, comprising a step of increasing the content of purine bases, by treating a ribonucleotide-containing material with nucleosidase; wherein free purine base ratio is more than 70% in the nucleic acid-based seasoning.

* * * * *